US007998718B2

(12) United States Patent
Gout et al.

(10) Patent No.: US 7,998,718 B2
(45) Date of Patent: Aug. 16, 2011

(54) IDENTIFICATION AND FUNCTIONAL CHARACTERIZATION OF A NOVEL RIBOSOMAL S6 PROTEIN KINASE

(75) Inventors: Ivan Gout, London (GB); Kenta Hara, Kobe (JP); Mike Waterfield, London (GB); Kazu Yonezawa, Kobe (JP)

(73) Assignee: Ludwig Institute for Cancer Research Ltd., New York, NY (US)

( * ) Notice: Subject to any disclaimer, the term of this patent is extended or adjusted under 35 U.S.C. 154(b) by 1408 days.

(21) Appl. No.: 11/004,840

(22) Filed: Dec. 7, 2004

(65) Prior Publication Data

US 2005/0158748 A1    Jul. 21, 2005

Related U.S. Application Data

(62) Division of application No. 09/762,258, filed as application No. PCT/US99/17595 on Aug. 4, 1999, now Pat. No. 6,830,909.

(60) Provisional application No. 60/095,268, filed on Aug. 4, 1998.

(51) Int. Cl.
*C12N 9/12* (2006.01)
*C07K 14/00* (2006.01)
*C12Q 1/48* (2006.01)
*C12P 21/00* (2006.01)
*C12N 15/00* (2006.01)
*C07H 21/00* (2006.01)

(52) U.S. Cl. ...... 435/194; 435/15; 435/320.1; 435/69.1; 530/350; 536/23.2; 536/23.5

(58) Field of Classification Search ............ 435/15, 435/194, 69.1, 320.1, 325, 252.3; 530/350; 536/23.2, 23.5
See application file for complete search history.

(56) References Cited

U.S. PATENT DOCUMENTS

| 5,932,445 A | 8/1999 | Lal et al. |
| 6,156,523 A | 12/2000 | Bandman et al. |
| 6,372,467 B1 * | 4/2002 | Blenis et al. ............ 435/194 |

FOREIGN PATENT DOCUMENTS

| WO | WO 9319752 | 10/1993 |
| WO | WO 9803662 | 1/1998 |
| WO | WO 9818935 | 5/1998 |
| WO | WO 9924463 | 5/1999 |

OTHER PUBLICATIONS

Branden et al., Introduction to Protein Structure, Garland Publishing Inc., New York, p. 247, 1991.*
Alessi, D.R., *The Protein Kinase Inhibitors Ro 318220 and GF 10903X are equally potent inhibitors of MAPKAP kinase-1 beta (Rsk-2)*, FEBS Lett. 402:121-3 (1997).
Alessi et al., *3-Phosphoinositide-Dependent Protein Kinase 1 (PDK1) Phosphorylates and Activates the p70 S6 Kinase In Vivo and In Vitro*, Current Biol. 8:69-81 (1997).
Boluyt et al., *Rapamycin Inhibits Alpha 1-adrenergic Receptor-stimulated cardiac myocyte hypertrophy but not activation of hypertrophy-associated genes. Evidence for involvement of p70 S6 kinase*, Circ. Res. 81:176-186 (1997).
Buckle et al., *HTLV-I-induced T-cell activation*, J. Acquir. Immune. Defic. Synd. Hum. Retrovirol. 13 Suppl. 1: S107-13 (1996).
Busca et al., *Inhibition of the Phosphatidylinositol 3-kinase/p70 (S6) kinase Pathway Induces B16 Melanoma Cell Differentiation*, J. Biol. Chem. 271:31824-31830 (1996).
Coolican et al., *The miogenic and myogenic actions of insulin-like growth factors utilize distinct signaling pathways*, J. Biol. Chem. 272:6653-6662 (1997).
Crawley et al., *Interleukin-10 Stimulation of Phosphatidylinositol 3-kinase and P70 S6 Kinase Is Required for the Proliferative but Not the Antiinflammatory Effects of the Cytokine*, J. Biol. Chem. 271:16357-16362 (1996).
Dennis et al., *The Principal Rapamycin-Sensitive $p70^{S6K}$ Phosphorylation Sites, T-229 and T-389, are Differentially Regulated by Rapamycin-Insensitive Kinase Kinases*, Mol. and Cell. Biol. 16:6242-6251 (1996).
Gout et al., *Molecular Cloning and Characterization of a Novel p70 S6 Kinase Containing a Proline-Rich Region*, J. Biol. Chem. 273:30061-30064 (1998).
Grove et al., *Cloning and Expression of Two Human P70 S6 kinase Polypeptides Differing Only at Their Amino Termini*, Mol. Cell. Biol. 11:5541-5550 (1991).
Flamigni et al., *Phosphatidylinositol 3-Kinase is Required for the Induction of Ornithine Decarboxylase in Leukemia Cells Stimulated to Growth*, Biochem Biopphys Res Comm 239: 729-33 (1997).
Han et al., *Rapamycin, Worthmannin and the Methylxanthine SQ20006 Inactivate p70S6K by Inducing Dephosphorylation of the Same Subset of Sites*, J. Biol. Chem. 270:21396-21403 (1995).
Hara et al., *Regulation of eIF-4E BP1 Phosphorylation by mTOR*, J. Biol. Chem. 272: 26457-63 (1997).
Kanda et al., *Phosphatidylinositol 3-Kinase-independent P70 S6 Kinase Activation by Fibroblast Growth Factor Receptor-1 Is Important for Proliferation but Not Differentiation of Endothelial Cells*, J. Biol. Chem. 272: 23347-23353 (1997).
Kawamata et al., *The Upregulation of p27Kip1 by Rapamycin Results in G1 Arrest in Exponentially growing T cell lines*, Blood 19: 561-9 (1998).
Kinoshita et al., *Raf/MAPK and Rapamycin-sensitive Pathways Mediate the Anti-apoptotic Function of p21Ras in IL-3-dependent Hematopoietic Cells*, Oncogene 15: 619-27 (1997).
Koyama et al., *Fibrillar Collagen Inhibits Arterial Smooth Muscle Proliferation Through Regulation of Cdk2 Inhibitors*, Cell 87:1069-1078 (1996).
Leighton et al., *Comparison of the Specificities of p70 S6 Kinase and MAPKAP Kinase-1 identifies a relatively specific substrate for p70 S6 kinase: the N-terminal Kinase Domain of MAPKAP Kinase-I is essential for Peptide Phosphorylation*, FEBS Letters 375: 289-293 (1995).

(Continued)

Primary Examiner — Delia Ramirez
(74) Attorney, Agent, or Firm — Morgan, Lewis & Bockius LLP

(57) ABSTRACT

A novel S6 kinase, $p70\beta^{S6k}$ is described, along with methods of making and using $p70\beta^{S6k}$ protein and related nucleic acids. The invention also discloses methods of identifying agents which modulate the activity of $p70\beta^{S6k}$ protein and/or its ligands.

11 Claims, 30 Drawing Sheets

OTHER PUBLICATIONS

Lin et al., *Heat Shock Activates c-Src tyrosine Kinases and Phosphatidylinoitol 3-kinase in NIH3T3 Fibroblasts*, J. Biol. Chem. 272:31196-31202 (1997).

Morreale et al., *Ro31-8220 Inhibits Protein Kinase C to Block the Phorbol Ester-stimulated Release of Choline and Ethanolamine-metabolites from C6 Glioma Cells: p70 S6 Kinase and MAPKAP Kinase-Ibeta Do Not Function Downstream of PKC in Activating PLD*, FEBS Letters 417:38-42 (1997).

Mukhopadhyay et al., *An Array of Insulin-Activated, Proline-Directed Serine/Threonine Kinases Phosphorylate the p70 S6 Kinase*, J. Biol. Chem. 267:3325-3335 (1995).

Pai et al., *Cross-linking CD28 leads to activation of 7-kDa S6 Kinase*, Eur. J. Immunol. 24:2364-2368 (1994).

Pearson et al., *The Principal Target of Rapamycin-Induced p70S6K Inactivation is a Novel Phosphorylation Site Within a Conserved Hydrophobic Domain*, EMBO J. 14:5279-5287 (1995).

Petritsch et al., *Selective Inhibition of p70 S6 Kinase Activation by Phosphatidylinositol 3-Kinase Inhibitors*, Eur. J. Biochem. 230:431-438 (1995).

Proud, *P70 S6 Kinase: an Engima With Variations*, TIBS Trends in Biochem. 21:181-185 (1996).

Pullen et al., *The Modular Phosphorylation and Activation of p70s6k*, FEBS Letters 410:78-82 (1997).

Saitoh et al., *Cloning and Characterization of $p70^{S6}$ Defines a Novel Family of p70 S6 Kinases*, Biochem. Biophys. Res. Commun. 253: 471-476 (1998).

Stewart et al., *Mitogenesis and Protein Synthesis: a role for Ribosomal Protein S6 Phosphorylation*, BioEssays 16: 809-815 (1994).

Weng et al., *Regulation of the p70 S6 Kinase by Phosphorylation In Vivo*, J. Biol. Chem. 273: 16621-16629 (1998).

Lee-Fruman et al., *Characterization of S6K2, a novel kinase homologous to S6K1*, Oncogene 18: 5108-5114 (1999).

Bork, *Powers and pitfalls in sequence analysis: the 70% hurdle*, Genome Research 10: 398-400 (2000).

Broun et al., *Catalytic plasticity of fatty acid modification enzymes underlying chemical diversity of plant lipids*, Science 282: 1315-1317 (1998).

Seffernick et al., *Melamine deaminase and atrazine chlorohydrolase: 98 percent identical but functionally different*, J. Bacteriol. 183: 2405-2410 (2001).

Van de Loo et al., *An oleate 12-hydroxylase from Ricinus communis L. is a fatty acyl desaturase homolog*, Proc. Natl. Acad. Sci: 92: 6743-6747 (1995).

Witkowski et al., *Conversion of a beta-ketoacyl synthase to a malonyl decarboxylase by replacement of the active-site cysteine with glutamine*, Biochemistry, 38: 11643-11650 (1999).

* cited by examiner

FIG. 1A

```
p70a.hum...    1    - - - - - - - - - - - - - - - - -GCACGAGGCTGGCGG       17
p70b.hum...    1    GAGAGAGAGAGAGAGAGAGAGAGGCTGGAGAGAG                      33 p70a.hum...   18    GTCCGGGCCCATGAGGCGACGAAGGCGAAGGAGGA                     50
p70b.hum...   34    AGAGAGAGAGAGAGAGAGGCGACGAGAGAGAGAGA                     66 p70a.hum...   51    CGGCTTTACCCAGCCCGGACTTCCGAG - - A                       80
p70b.hum...   67    CTCGTGCCGAATGGCCACGGCCGACGGCCCG                         99 p70a.hum...   81    CAGGAAGCTGAGGACATGGCAGGAGTGTTTGA                       113
p70b.hum...  100    CGGGCCGGCCGGCCATGGCGGCCGTGTTTGA                        132 p70a.hum...  114    CATAGACCTGGACCAGGAGGACGCGGCTC                          146
p70b.hum...  133    TTTGGATTTGGAGACGGAGGAAGGCAGCGAGGG                      165 p70a.hum...  147    TGAGGATGAGCTGGAGGAGGGGTCAGTTAAA                        179
p70b.hum...  166    CGAGGGCGGAGCCAGA - - - - - -GCTCAGCCCCG                 191
```

FIG. 1B

```
p70a.hum... 180  TGAAAGCATGGACCATGGGGGAGTT---GGAC  208
p70b.hum... 192  CGGACGCATGTCCCCTTGCCGAGTTGAGGCAG  224 p70a.hum... 209  CATGAAACTTGGCATGGAACATTGTGAGAAAT  241
p70b.hum... 225  CTGCCTAGAGCCTGTGGGACACTATGAAGAGG  257 p70a.hum... 242  TTGAAATCTCAGAACTAGTGTGAACAGAGGGC  274
p70b.hum... 258  TGGAGCTGACTGAGACCAGCGTGAACGTTGGCC  290 p70a.hum... 275  CAGAAAAATCAGACCAGAATGTTTTGAGCTAC  307
p70b.hum... 291  CAGAGCGCATCGGGCCCACTGCTTTGAGCTGC  323 p70a.hum... 308  TTCGGGTACTTGGTAAAGGGGGCTATGGAAAGG  340
p70b.hum... 324  TGCGTGTGCTGGGCAGGGGGGGCTATGGCAAGG  356 p70a.hum... 341  TTTTCAAGTACGAAAAGTAACAGGAGCAATA  373
p70b.hum... 357  TGTTCCAGGTGCGAAAGGTGCAAGGCACCACT  389
```

FIG. IC

| | | | | | | | |
|---|---|---|---|---|---|---|---|
| p70a.hum... | 374 | CTGGGAAAATATTTGCCATGAAGAAGGTGCTTAAA | 406 |
| p70b.hum... | 390 | TGGGCAAAATATATGCCATGAAAGAAAGTCCTAAGGA | 422 |
| p70a.hum... | 407 | AGGCAATGATAGTAAGAAATGCTAAGATACAG | 439 |
| p70b.hum... | 423 | AGGCAACAAATTGTGCGCAAGGACACAG | 455 |
| p70a.hum... | 440 | CTCATACAAAGCAAGAACGGAATATTCTGGAGG | 472 |
| p70b.hum... | 456 | CACACACGGGCTGAGCGGAACATTCTAGAGT | 488 |
| p70a.hum... | 473 | AAGTAAAGCATCCCTTCATCGTGGATTTAATTT | 505 |
| p70b.hum... | 489 | CAGTGAAGCACCCCTTTATTGTGGAACTGGCCT | 521 |
| p70a.hum... | 506 | ATGCCTTTCAGACTGGTGGAAAACTCTACCTCA | 538 |
| p70b.hum... | 522 | ATGCCTTCCAGACTGGTGGCAAACTCTACCTCA | 554 |
| p70a.hum... | 539 | TCCTTGAGTATCTCAGTGGAGGAGAACTATTTA | 571 |
| p70b.hum... | 555 | TCCTTGAGTGCCTCAGTGGTGGCGAGCTCTTCA | 587 |

FIG. ID

| | | | | | | | | |
|---|---|---|---|---|---|---|---|---|
| p70a.hum... 572 | TGCAGTT | AGAAGAGGA | ATATTT | ATGGAAG | 604 |
| p70b.hum... 588 | CGCATCT | GGAGAGGG | CATCTT | CCTGGAAG | 620 |

| p70a.hum... 605 | ACACTGCCTGCTT | TACTTGGC | AGAATCT | CCA | 637 |
| p70b.hum... 621 | ATACGGCCTGCTT | CTACCTGGC | TGAGATCA | CGC | 653 |

| p70a.hum... 638 | TGGCTTTGGG | GCATT | ACATCAAA | AGGGATCA | 670 |
| p70b.hum... 654 | TGGCCCTGGG | CCATC | CCACTCCC | AGGCATCA | 686 |

| p70a.hum... 671 | TCTACAGAGACCTG | AAGCCG | GAGAATA | TCATGC | 703 |
| p70b.hum... 687 | TCTACCGGACCTC | AAGCCC | GAGAACA | CATCATGC | 719 |

| p70a.hum... 704 | TTAATCACCA | AGGTCATG | TGAAACT | AACAGACT | 736 |
| p70b.hum... 720 | TCAGCAGCCA | GGGCCACA | TCAAACT | GACCGACT | 752 |

| p70a.hum... 737 | TTGGACTA | TGCAAAGA | ATCTATT | CATGATGGAA | 769 |
| p70b.hum... 753 | TTGGACTC | TGCAAGGA | GTCTATC | CATGAGGGCG | 785 |

FIG. IE

```
p70a.hum...  770  CAGTCACACACAATTTGTGAACAATAGAAT  802
p70b.hum...  786  CCGTCACTCACACCTTCTGCGGCACCATGAGT  818 p70a.hum...  803  ACATGGCCCCTGAAGAGAAGTGGCC  835
p70b.hum...  819  ACATGGCCCCCTGAGATTCTGGTGCGCAGTGGCC  851 p70a.hum...  836  ACAATCGTGCTGTGGATTGGTGGAGTTTGGGAG  868
p70b.hum...  852  ACAACCGGCTGTGTGGACTGGTGGAGCCTGGGG  884 p70a.hum...  869  CATTAATGTATGACATGCTGACTGGAGCACCC  901
p70b.hum...  885  CCCTGATGTACGACATGCTCACTGGATCGCCG  917 p70a.hum...  902  CATTCACTGGGAGAATAGAAAGAAAACAATTG  934
p70b.hum...  918  CCTTACCGCAGAGAAGAAGAAAACCATGG  950 p70a.hum...  935  ACAAATCCTCAAATGTAAACTCAATTGCCTC  967
p70b.hum...  951  ATAAGATCATCAGGGCAAGCTGGCACTGCCC  983
```

FIG. 1F

```
p70a.hum...  968  CCTACCTCACACAAGCCAGAGAAGATCTGCTTA  1000
p70b.hum...  984  CCTACCTCACCCTGCCCCGGGACCTTGTCA     1016 p70a.hum... 1001  AAAAGCTGCTGAAAAGAAATGCTGCTTCTCGTC  1033
p70b.hum... 1017  AAAAGTTTCTGAAACGGAATCCCAGCCAGCGGA  1049 p70a.hum... 1034  TGGAGCTGGTCCTGGGGACGCTGGAGAAGTTC   1066
p70b.hum... 1050  TTGGGGTGGCCCCAGGGATGCTGGATGTGC     1082 p70a.hum... 1067  AAGCTCATCCATTCTTTAGACACATTAACTGGG  1099
p70b.hum... 1083  AGAGACATCCCTTTTTCCGGCACACGAATTGGG  1115 p70a.hum... 1100  AAGAACTTCTGGTCTCGAAAGGTGGAGCCCCT   1132
p70b.hum... 1116  ACGACCTTCTGGCCTGGACGTGTGGAGCCCCT   1148 p70a.hum... 1133  TTAACCTCTGTTGCAATCTGAAGAGGATGTAA   1165
p70b.hum... 1149  TCAGGCCCTGTCTGCAGTCAGAGGAGACGTGA   1181
```

FIG. 1G

```
p70a.hum... 1166  GTCAGTTTGATTCCAAGTTTACACGTCAGACAC  1198
p70b.hum... 1182  GCCAGTTTGATACCCGCTTCACACGGCAGACGC  1214 p70a.hum... 1199  CTGTCGACAGCCCAGATGACTCAACTCTCAGTG  1231
p70b.hum... 1215  CGGTGGACAGTCCCTGATGACAGCCCTCAGCG   1247 p70a.hum... 1232  AAGTGCCAATTCAGGTCTTTCTGGGTTTACAT   1264
p70b.hum... 1248  AGAGTGCCAACCCGGTCTGTCCTGGGCTTACAT  1280 p70a.hum... 1265  ATGTGGCTTCCATTCTGTACTTGAAAGTGAAAG  1297
p70b.hum... 1281  ACGTGGCGCCGGCCGTCCTGGACAGCATCAAGG  1313 p70a.hum... 1298  AAAGTTTCCTTTGAACCAAAAATCCGATCAC    1330
p70b.hum... 1314  AGGGCTCTTCTTCCAGCCCAAGCTGCGCTCAC   1346 p70a.hum... 1331  CTCGAAGATTATTGGCAGCCACGAACACCTG    1363
p70b.hum... 1347  CCAGGCGCCTCAACAGTAGCCCCCGGTCCCG    1379
```

FIG. 1H

```
p70a.hum... 1364  TCAGCCCAGTCAAATTTCTCCT---GGGAT  1392
p70b.hum... 1380  TCAGCCCCTCAAGTTCTCCCTTTGAGGGT  1412 p70a.hum... 1393  TTCTGGGAAGAGGTGCTCGGCCAGCACAGCA  1425
p70b.hum... 1413  TTCGGCCCAGCAGCCTGCCGGAGCCACGG   1445 p70a.hum... 1426  AATCCTCAGACACCTGTGGAATACCAATGGAA  1458
p70b.hum... 1446  AGCTACCTCTACCTCCACTCCTGCCACCGCCGC  1478 p70a.hum... 1459  ACAAGTGGCATAGAGAGATGGATGTGACAATG  1491
p70b.hum... 1479  CGCCCTCGACCCACCGCCCCCTCCCCATCCGTC  1511 p70a.hum... 1492  AGTGGGAAGCATCGGCACCACTTCCAATACGA  1524
p70b.hum... 1512  CCCCCTCAGGA---CCAAGAAGTCCAAGAGGG  1541 p70a.hum... 1525  CAGCCGAACTCTGGCCATACAAAACAAGCT  1557
p70b.hum... 1542  GCCGTGGGCCAGGCCGCTAGGAAGCGGGT   1574
```

FIG. 11

```
p70a.hum... 1558  T T T C C A T G A T C T C C A A A C G G C C A G A G C A C C T G  1590
p70b.hum... 1575  G G G G T G A G G G T A G C C C T T G A G C C T G T C C T G      1607 p70a.hum... 1591  C G T A T G A A T C T A T G A C A G A G C A A T G C T T T T A A T  1623
p70b.hum... 1608  C G G C T G T G A G A G C A G G A C C C T G G G C C A G T T      1640 p70a.hum... 1624  G A A T T T A G G C A A A A A G G T G G A G G G A G A T G T      1656
p70b.hum... 1641  C C A G A G C C T G G G G G T G T C T G G G G G T            1673 p70a.hum... 1657  G T G A G C A T C C T G C A A G G T G A A A C A A G A C T C A A A  1689
p70b.hum... 1674  G T G A G T G C G T A T G A A A G T G T C T G C T G G G G      1706 p70a.hum... 1690  A T G A C A G T T T C A G A G A G T C A T T A C A T A          1722
p70b.hum... 1707  C A G - C T G T G C C C C T G A A T C A T G G C A C G G A G G G  1738 p70a.hum... 1723  G A A C A C T T C G G A C A C - - A G G A A A A T A A A C G T G  1753
p70b.hum... 1739  C C G C C C G C C A C A C C C G C G C T C A A C T G C T C C C G  1771
```

FIG. 1J

```
p70a.hum... 1754  GATTTT AAAA  TCAA TCAATGGT CAAAAAA  1786
p70b.hum... 1772  TGGAAGA TTAAG GCT GAATCATGA AAAAAAA  1804 p70a.hum... 1787  AA CTT AAAG CA AAATAGTATTGCTGAACTCTTA    1819
p70b.hum... 1805     AA AAAA AAAA                         1816 p70a.hum... 1820  GGCACATCAATTAATTGATTCCTCGCGACATCT         1852 p70a.hum... 1853  TTCTCAACCTTATCAAGGATTTTCATGTTGATG         1885 p70a.hum... 1886  ACTCGAAACTGACAGTATTAAGGGTAGGATGTT         1918 p70a.hum... 1919  GCTCTGAATCACTCACTGTGAGTCTGATGTGTGAAGA     1951
```

FIG. 1K

```
p70a.hum... 1952   AGGGTATCCTTTCATTAGGCAAGTACAAATTGC  1984
p70a.hum... 1985   CTATAATACTTGCAAACTAAGGACAAATTAGCAT 2017
p70a.hum... 2018   GCAAGCTTGGTCAAACTTTTCCCAGGCAAAATG  2050
p70a.hum... 2051   GGAAGGCAAAGACAAAAGAAACTTACCAATTGA  2083
p70a.hum... 2084   TGTTTTACGTGCAAACAACCTGAATCTTTTTTT  2116
p70a.hum... 2117   TATATAAATATATATTTTTCAAATAGATTTTTG  2149
```

FIG. 1L

| | | |
|---|---|---|
| p70a.hum... 2150 | ATTCAGCTCATTATGAAAAACATCCCAAACTTT | 2182 |
| p70a.hum... 2183 | AAAATGCGAAATTATTGGTTGGTGTGAAGAAAG | 2215 |
| p70a.hum... 2216 | CCAGACAACTTCTGTTTCTTCTTGGTGAAAT | 2248 |
| p70a.hum... 2249 | AATAAAAATGCAAATGAATCATTGTTAACACAGC | 2281 |
| p70a.hum... 2282 | TGTGGCTCGTTTGAGGGATTGGGGTGGACCTGG | 2314 |
| p70a.hum... 2315 | GGTTTATTTTCAGTAACCCAGCTGCGGAGCCT | 2346 |

FIG. 2A-1

```
p70a.Prot.t...    1  M R R R R R R D G F Y P A P D F R H R E A E D M A G V F D I D L D   33
p70b.Prot.t...    1  - - - - - - - M A R G R R A R G A G A A M A A V F D L D L E       23 p70a.Prot.t...   34  Q P E D A G S E D E L E G G Q L N E S M D H G G V G P Y E L G M   66
p70b.Prot.t...   24  T E E G S E G E G E P E L S P A D A C P L A E L R A A G L E - P V   55 p70a.Prot.t...   67  E H C E K F E I S E T S V N R G P E K I R P E C F E L L R V L G K   99
p70b.Prot.t...   56  G H Y E E V E L T E T S V N V G P E R I G P H C F E L L R V L G K   88 p70a.Prot.t...  100  G G Y G K V F Q V R K V T G A N T G K I F A M K V L K K A M I V R  132
p70b.Prot.t...   89  G G Y G K V F Q V R K V Q G T N L G K I Y A M K V L R K A K I V R  121 p70a.Prot.t...  133  N A K D T A H T K A E R N I L E E V K H P F I V D L I Y A F Q T G  165
p70b.Prot.t...  122  N A K D T A H T R A E R N I L E S V K H P F I V E L A Y A F Q T G  154 p70a.Prot.t...  166  G K L Y L I L E Y L S G G E L F M Q L E R E G I F M E D T A C F Y  198
p70b.Prot.t...  155  G K L Y L I L E C L S G G E L F T H L E R E G I F L E D T A C F Y  187
```

FIG. 2A-2

```
p70a.Prot.t... 199  LAEIS MALGHLHQKG IIYRDLKPENIMLN HQGH 231
p70b.Prot.t... 188  LAEIT LALGHLHSQG IIYRDLKPENIMLS SQGH 220 p70a.Prot.t... 232  VKLTDFGLCKES IHDG TVTHTFCGTIEYMAPEI 264
p70b.Prot.t... 221  IKLTDFGLCKES IHEG AVTHTFCGTIEYMAPEI 253 p70a.Prot.t... 265  LMRSGHNRAVDWWSLGALMYDMLTGA PPFTGEN 297
p70b.Prot.t... 254  LVRSGHNRAVDWWSLGALMYDMLTGS PPFTAEN 286 p70a.Prot.t... 298  RKKT IDKI LKCKLN LPPYLTQ EARDL LKKLLKR 330
p70b.Prot.t... 287  RKKT MDKI IRGKLA LPPYLTPD ARDL VKKFLKR 319 p70a.Prot.t... 331  NAASRL GAGPGDAGE VQA HPFFRH INWEELLAR 363
p70b.Prot.t... 320  NPSQRI GGGPGDADV QR HPFFRH MNWDDLLAW 352 p70a.Prot.t... 364  KVERPFK PLLQSEEDVSQFDS KFTRQTPVDSPD 396
p70b.Prot.t... 353  RVDPPFR PCLQSEEDVSQFDT RFTRQTPVDSPD 385
```

FIG. 2A-3

```
p70a.Prot.t...  397  D S T L S E S A N Q V F L G F T Y V A P S V L E S V K E K F S F E   429
p70b.Prot.t...  386  D T A L S E S A N Q A F L G F T Y V A P S V L D S I K E G F S F Q   418 p70a.Prot.t...  430  P K I R S P R R F I G S P R T P V S P V K F S P G D F W G R G A S   462
p70b.Prot.t...  419  P K L R S P R R L N S S P R V P V S P L K F S P - - F E G F R P S   449 p70a.Prot.t...  463  A S T A N P Q T P V E Y P M E T S G I E Q M D V T T S G E A S A P   495
p70b.Prot.t...  450  P S - L - P E - P T E L P L - P P - L - - L P P P P - S T T A P   474 p70a.Prot.t...  496  L P I R Q P N S G P Y K K Q A F P M I S K R P E H L R M N L         525
p70b.Prot.t...  475  L P I R P P S G T K K S K R G R P G R                                495
```

SEQUENCE IDENTITY BETWEEN p70α AND p70β ISOFORMS

Expression pattern of the p70β mRNAs in tumour cell lines

1 Promyelocytic leukemia HL-60
2 HeLa cell S3
3 chronic myelogenous leukemia K562
4 Lymphoblastic leukemia MOLT-4
5 Burkitt's lymphoma Raji
6 colorectal adenocarcinoma SW480
7 Lung carcinoma A549
8 Melanoma G361

FIG. 4A
Autoradiography
anti-Flag blot

PHOSPHORYLATION OF THE RIBOSOMAL S6 PROTEIN C-TERMINAL PEPTIDES BY p70α AND β KINASES

ACTIVATION OF THE P70α AND β KINASES IN RESPONSE TO VARIOUS STIMULI IN VIVO

1 MOCK TRANSFECTION
2 p70α (STARVED AND NONTREATED)
3 p70α (STARVED AND INSULIN STIMULATED)
4 p70β (STARVED AND NONTREATED)
5 p70β (STARVED AND INSULIN STIMULATED)
6 p70β (STARVED AND SERUM STIMULATED)
7 p70β (STARVED AND TPA STIMULATED)

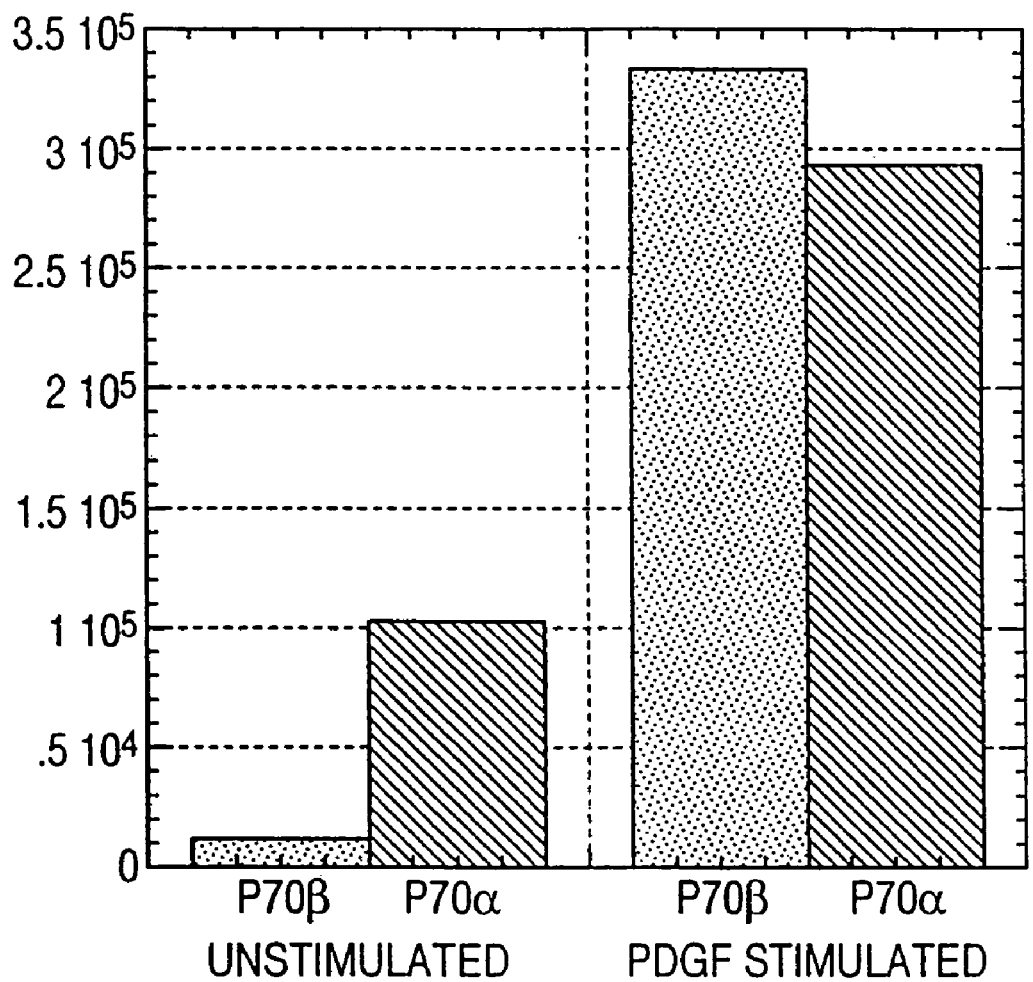

FIG. 6A
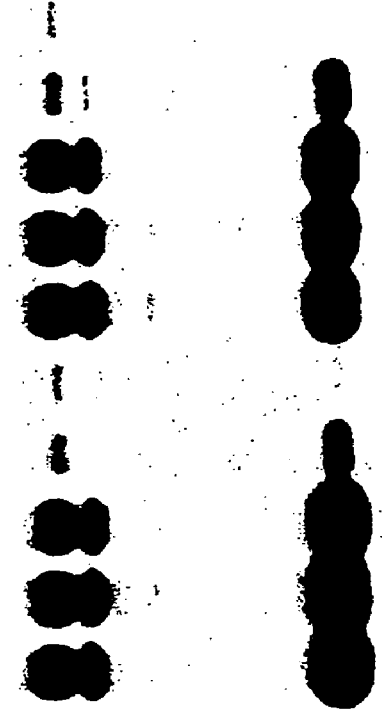
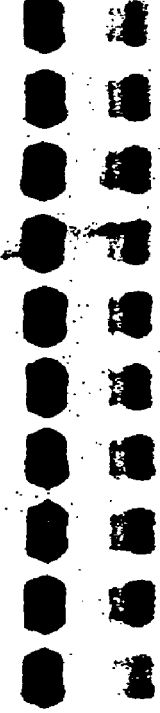
Autoradiography
anti-Flag blot

| Rapamycin (nM) | 0 | 0.2 | 2 | 20 | 200 | 0 | 0 | 0 | 0 | 0 |
| --- | --- | --- | --- | --- | --- | --- | --- | --- | --- | --- |
| Wortmannin (nM) | 0 | 0 | 0 | 0 | 0 | 0 | 1 | 10 | 100 | 1000 |

Autoradiography            anti-Flag blot

INTERACTION OF P70S6K β WITH DIFFERENT GST/SH3 FUSION PROTEINS IN VITRO

IMMUNOPRECIPATATION AND WESTERN BLOT ANALYSIS OF P70βI AND βII TRANSIENTLY OVEREXPRESSED IN HEK 293 CELLS 1-mock transfection
2-Flag-p70αI
3-Flag-p70βI
4-Flag-p70βII FIG. 9 A MODEL FOR THE ACTIVATION OF THE p70S6 KINASE

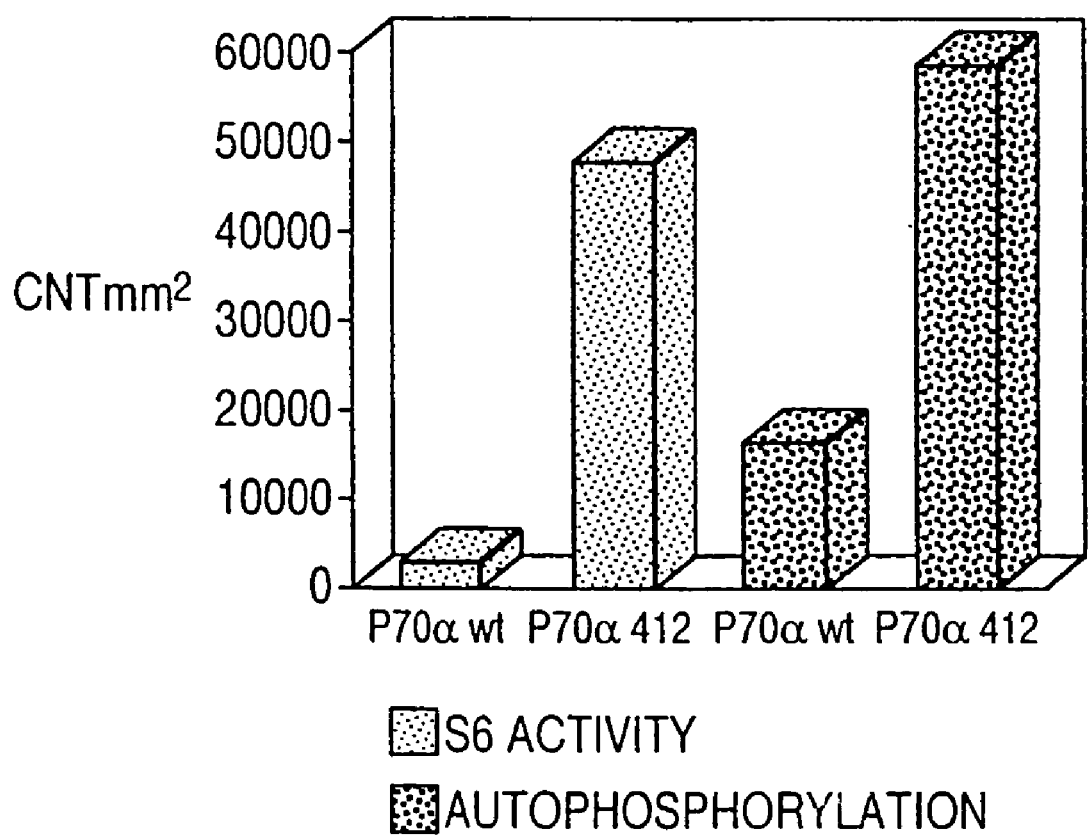

SEQUENCE LISTING

```
<160> NUMBER OF SEQ ID NOS: 8

<210> SEQ ID NO 1
<211> LENGTH: 1816
<212> TYPE: DNA
<213> ORGANISM: Homo sapiens
<220> FEATURE:
<221> NAME/KEY: CDS
<222> LOCATION: (77)..(1561)
<223> OTHER INFORMATION: p70(beta) S6 Kinase gene

<400> SEQUENCE: 1
gagagagaga gagagagaga gagagagaga gagagagaga gagagagaga gagagagaga        60
gagagactcg tgccga atg gca cga ggc cga cgg gcc cgc ggg gcc ggc gcc       112
                Met Ala Arg Gly Arg Arg Ala Arg Gly Ala Gly Ala
                  1               5                  10
```

```
gcc atg gcg gcc gtg ttt gat ttg gat ttg gag acg gag gaa ggc agc      160
Ala Met Ala Ala Val Phe Asp Leu Asp Leu Glu Thr Glu Glu Gly Ser
        15                  20                  25 gag ggc gag ggc gag cca gag ctc agc ccc gcg gac gca tgt ccc ctt      208
Glu Gly Glu Gly Glu Pro Glu Leu Ser Pro Ala Asp Ala Cys Pro Leu
 30                  35                  40 gcc gag ttg agg gca gct ggc cta gag cct gtg gga cac tat gaa gag      256
Ala Glu Leu Arg Ala Ala Gly Leu Glu Pro Val Gly His Tyr Glu Glu
 45                  50                  55                  60 gtg gag ctg act gag acc agc gtg aac gtt ggc cca gag cgc atc ggg      304
Val Glu Leu Thr Glu Thr Ser Val Asn Val Gly Pro Glu Arg Ile Gly
                 65                  70                  75 ccc cac tgc ttt gag ctg ctc cgt gtg ctg ggc aag ggg ggc tat ggc      352
Pro His Cys Phe Glu Leu Leu Arg Val Leu Gly Lys Gly Gly Tyr Gly
             80                  85                  90 aag gtg ttc cag gtg cga aag gtg caa ggc acc aac ttg ggc aaa ata      400
Lys Val Phe Gln Val Arg Lys Val Gln Gly Thr Asn Leu Gly Lys Ile
         95                  100                 105 tat gcc atg aaa gtc cta agg aag gcc aaa att gtg cgc aat gcc aag      448
Tyr Ala Met Lys Val Leu Arg Lys Ala Lys Ile Val Arg Asn Ala Lys
     110                 115                 120 gac aca gca cac aca cgg gct gag cgg aac att cta gag tca gtg aag      496
Asp Thr Ala His Thr Arg Ala Glu Arg Asn Ile Leu Glu Ser Val Lys
125                 130                 135                 140 cac ccc ttt att gtg gaa ctg gcc tat gcc ttc cag act ggt ggc aaa      544
His Pro Phe Ile Val Glu Leu Ala Tyr Ala Phe Gln Thr Gly Gly Lys
                 145                 150                 155 ctc tac ctc atc ctt gag tgc ctc agt ggt ggc gag ctc ttc acg cat      592
Leu Tyr Leu Ile Leu Glu Cys Leu Ser Gly Gly Glu Leu Phe Thr His
             160                 165                 170 ctg gag cga gag ggc atc ttc ctg gaa gat acg gcc tgc ttc tac ctg      640
Leu Glu Arg Glu Gly Ile Phe Leu Glu Asp Thr Ala Cys Phe Tyr Leu
         175                 180                 185 gct gag atc acg ctg gcc ctg ggc cat ctc cac tcc cag ggc atc atc      688
Ala Glu Ile Thr Leu Ala Leu Gly His Leu His Ser Gln Gly Ile Ile
     190                 195                 200 tac cgg gac ctc aag ccc gag aac atc atg ctc agc agc cag ggc cac      736
Tyr Arg Asp Leu Lys Pro Glu Asn Ile Met Leu Ser Ser Gln Gly His
205                 210                 215                 220 atc aaa ctg acc gac ttt gga ctc tgc aag gag tct atc cat gag ggc      784
Ile Lys Leu Thr Asp Phe Gly Leu Cys Lys Glu Ser Ile His Glu Gly
                 225                 230                 235 gcc gtc act cac acc ttc tgc ggc acc att gag tac atg gcc cct gag      832
Ala Val Thr His Thr Phe Cys Gly Thr Ile Glu Tyr Met Ala Pro Glu
             240                 245                 250 att ctg gtg cgc agt ggc cac aac cgg gct gtg gac tgg tgg agc ctg      880
Ile Leu Val Arg Ser Gly His Asn Arg Ala Val Asp Trp Trp Ser Leu
         255                 260                 265 ggg gcc ctg atg tac gac atg ctc act gga tcg ccg ccc ttt acc gca      928
Gly Ala Leu Met Tyr Asp Met Leu Thr Gly Ser Pro Pro Phe Thr Ala
     270                 275                 280 gag aac cgg aag aaa acc atg gat aag atc atc agg ggc aag ctg gca      976
Glu Asn Arg Lys Lys Thr Met Asp Lys Ile Ile Arg Gly Lys Leu Ala
285                 290                 295                 300 ctg ccc ccc tac ctc acc cca gat gcc cgg gac ctt gtc aaa aag ttt     1024
Leu Pro Pro Tyr Leu Thr Pro Asp Ala Arg Asp Leu Val Lys Lys Phe
                 305                 310                 315 ctg aaa cgg aat ccc agc cag cgg att ggg ggt ggc cca ggg gat gct     1072
Leu Lys Arg Asn Pro Ser Gln Arg Ile Gly Gly Gly Pro Gly Asp Ala
             320                 325                 330
```

```
gct gat gtg cag aga cat ccc ttt ttc cgg cac atg aat tgg gac gac      1120
Ala Asp Val Gln Arg His Pro Phe Phe Arg His Met Asn Trp Asp Asp
        335                 340                 345 ctt ctg gcc tgg cgt gtg gac ccc cct ttc agg ccc tgt ctg cag tca      1168
Leu Leu Ala Trp Arg Val Asp Pro Pro Phe Arg Pro Cys Leu Gln Ser
350                 355                 360 gag gag gac gtg agc cag ttt gat acc cgc ttc aca cgg cag acg ccg      1216
Glu Glu Asp Val Ser Gln Phe Asp Thr Arg Phe Thr Arg Gln Thr Pro
365                 370                 375                 380 gtg gac agt cct gat gac aca gcc ctc agc gag agt gcc aac cag gcc      1264
Val Asp Ser Pro Asp Asp Thr Ala Leu Ser Glu Ser Ala Asn Gln Ala
                385                 390                 395 ttc ctg ggc ttc aca tac gtg gcg ccg tct gtc ctg gac agc atc aag      1312
Phe Leu Gly Phe Thr Tyr Val Ala Pro Ser Val Leu Asp Ser Ile Lys
    400                 405                 410 gag ggc ttc tcc ttc cag ccc aag ctg cgc tca ccc agg cgc ctc aac      1360
Glu Gly Phe Ser Phe Gln Pro Lys Leu Arg Ser Pro Arg Arg Leu Asn
415                 420                 425 agt agc ccc cgg gtc ccc gtc agc ccc ctc aag ttc tcc cct ttt gag      1408
Ser Ser Pro Arg Val Pro Val Ser Pro Leu Lys Phe Ser Pro Phe Glu
430                 435                 440 ggg ttt cgg ccc agc ccc agc ctg ccg gag ccc acg gag cta cct cta      1456
Gly Phe Arg Pro Ser Pro Ser Leu Pro Glu Pro Thr Glu Leu Pro Leu
445                 450                 455                 460 cct cca ctc ctg cca ccg ccg ccc tcg acc acc gcc cct ctc ccc          1504
Pro Pro Leu Leu Pro Pro Pro Pro Ser Thr Thr Ala Pro Leu Pro
                465                 470                 475 atc cgt ccc ccc tca ggg acc aag aag tcc aag agg ggc cgt ggg cgt      1552
Ile Arg Pro Pro Ser Gly Thr Lys Lys Ser Lys Arg Gly Arg Gly Arg
                480                 485                 490 cca ggg cgc taggaagccg ggtggggggtg agggtagccc ttgagccctg             1601
Pro Gly Arg
    495 tccctgcggc tgtgagagca gcaggaccct gggccagttc cagagacctg ggggtgtgtc    1661 tgggggtggg gtgtgagtgc gtatgaaagt gtgtgtctgc tggggcagct gtgcccctga    1721 atcatgggca cggagggccg cccgccacac cccgcgctca actgctcccg tggaagatta    1781 aagggctgaa tcatgaaaaa aaaaaaaaaa aaaaa                               1816

<210> SEQ ID NO 2
<211> LENGTH: 495
<212> TYPE: PRT
<213> ORGANISM: Homo sapiens
<220> FEATURE:
<223> OTHER INFORMATION: p70(beta) S6 Kinase protein

<400> SEQUENCE: 2

Met Ala Arg Gly Arg Arg Ala Arg Gly Ala Gly Ala Ala Met Ala Ala
1               5                   10                  15

Val Phe Asp Leu Asp Leu Glu Thr Glu Glu Gly Ser Glu Gly Glu Gly
                20                  25                  30

Glu Pro Glu Leu Ser Pro Ala Asp Ala Cys Pro Leu Ala Glu Leu Arg
            35                  40                  45

Ala Ala Gly Leu Glu Pro Val Gly His Tyr Glu Val Glu Leu Thr
        50                  55                  60

Glu Thr Ser Val Asn Val Gly Pro Glu Arg Ile Gly Pro His Cys Phe
65                  70                  75                  80

Glu Leu Leu Arg Val Leu Gly Lys Gly Gly Tyr Gly Lys Val Phe Gln
                85                  90                  95
```

-continued

Val Arg Lys Val Gln Gly Thr Asn Leu Gly Lys Ile Tyr Ala Met Lys
            100                 105                 110

Val Leu Arg Lys Ala Lys Ile Val Arg Asn Ala Lys Asp Thr Ala His
            115                 120                 125

Thr Arg Ala Glu Arg Asn Ile Leu Glu Ser Val Lys His Pro Phe Ile
        130                 135                 140

Val Glu Leu Ala Tyr Ala Phe Gln Thr Gly Gly Lys Leu Tyr Leu Ile
145                 150                 155                 160

Leu Glu Cys Leu Ser Gly Gly Glu Leu Phe Thr His Leu Glu Arg Glu
                165                 170                 175

Gly Ile Phe Leu Glu Asp Thr Ala Cys Phe Tyr Leu Ala Glu Ile Thr
            180                 185                 190

Leu Ala Leu Gly His Leu His Ser Gln Gly Ile Ile Tyr Arg Asp Leu
        195                 200                 205

Lys Pro Glu Asn Ile Met Leu Ser Ser Gln Gly His Ile Lys Leu Thr
    210                 215                 220

Asp Phe Gly Leu Cys Lys Glu Ser Ile His Glu Gly Ala Val Thr His
225                 230                 235                 240

Thr Phe Cys Gly Thr Ile Glu Tyr Met Ala Pro Glu Ile Leu Val Arg
                245                 250                 255

Ser Gly His Asn Arg Ala Val Asp Trp Trp Ser Leu Gly Ala Leu Met
            260                 265                 270

Tyr Asp Met Leu Thr Gly Ser Pro Pro Phe Thr Ala Glu Asn Arg Lys
        275                 280                 285

Lys Thr Met Asp Lys Ile Ile Arg Gly Lys Leu Ala Leu Pro Pro Tyr
    290                 295                 300

Leu Thr Pro Asp Ala Arg Asp Leu Val Lys Lys Phe Leu Lys Arg Asn
305                 310                 315                 320

Pro Ser Gln Arg Ile Gly Gly Gly Pro Gly Asp Ala Ala Asp Val Gln
                325                 330                 335

Arg His Pro Phe Phe Arg His Met Asn Trp Asp Asp Leu Leu Ala Trp
            340                 345                 350

Arg Val Asp Pro Pro Phe Arg Pro Cys Leu Gln Ser Glu Glu Asp Val
        355                 360                 365

Ser Gln Phe Asp Thr Arg Phe Thr Arg Gln Thr Pro Val Asp Ser Pro
    370                 375                 380

Asp Asp Thr Ala Leu Ser Glu Ser Ala Asn Gln Ala Phe Leu Gly Phe
385                 390                 395                 400

Thr Tyr Val Ala Pro Ser Val Leu Asp Ser Ile Lys Glu Gly Phe Ser
                405                 410                 415

Phe Gln Pro Lys Leu Arg Ser Pro Arg Arg Leu Asn Ser Ser Pro Arg
            420                 425                 430

Val Pro Val Ser Pro Leu Lys Phe Ser Pro Phe Glu Gly Phe Arg Pro
        435                 440                 445

Ser Pro Ser Leu Pro Glu Pro Thr Glu Leu Pro Leu Pro Pro Leu Leu
    450                 455                 460

Pro Pro Pro Pro Pro Ser Thr Thr Ala Pro Leu Pro Ile Arg Pro Pro
465                 470                 475                 480

Ser Gly Thr Lys Lys Ser Lys Arg Gly Arg Gly Arg Pro Gly Arg
                485                 490                 495

<210> SEQ ID NO 3
<211> LENGTH: 2346
<212> TYPE: DNA
<213> ORGANISM: Homo sapiens

```
<220> FEATURE:
<221> NAME/KEY: CDS
<222> LOCATION: (28)..(1602)
<223> OTHER INFORMATION: p70(alpha) S6 Kinase gene

<400> SEQUENCE: 3
gcacgaggct gcggcgggtc cgggccc atg agg cga cga agg agg cgg gac ggc        54
                                Met Arg Arg Arg Arg Arg Arg Asp Gly
                                1               5 ttt tac cca gcc ccg gac ttc cga gac agg gaa gct gag gac atg gca         102
Phe Tyr Pro Ala Pro Asp Phe Arg Asp Arg Glu Ala Glu Asp Met Ala
 10              15                  20                  25 gga gtg ttt gac ata gac ctg gac cag cca gag gac gcg ggc tct gag         150
Gly Val Phe Asp Ile Asp Leu Asp Gln Pro Glu Asp Ala Gly Ser Glu
             30                  35                  40 gat gag ctg gag gag ggg ggt cag tta aat gaa agc atg gac cat ggg         198
Asp Glu Leu Glu Glu Gly Gly Gln Leu Asn Glu Ser Met Asp His Gly
         45                  50                  55 gga gtt gga cca tat gaa ctt ggc atg gaa cat tgt gag aaa ttt gaa         246
Gly Val Gly Pro Tyr Glu Leu Gly Met Glu His Cys Glu Lys Phe Glu
     60                  65                  70 atc tca gaa act agt gtg aac aga ggg cca gaa aaa atc aga cca gaa         294
Ile Ser Glu Thr Ser Val Asn Arg Gly Pro Glu Lys Ile Arg Pro Glu
 75                  80                  85 tgt ttt gag cta ctt cgg gta ctt ggt aaa ggg ggc tat gga aag gtt         342
Cys Phe Glu Leu Leu Arg Val Leu Gly Lys Gly Gly Tyr Gly Lys Val
 90                  95                 100                 105 ttt caa gta cga aaa gta aca gga gca aat act ggg aaa ata ttt gcc         390
Phe Gln Val Arg Lys Val Thr Gly Ala Asn Thr Gly Lys Ile Phe Ala
            110                 115                 120 atg aag gtg ctt aaa aag gca atg ata gta aga aat gct aaa gat aca         438
Met Lys Val Leu Lys Lys Ala Met Ile Val Arg Asn Ala Lys Asp Thr
        125                 130                 135 gct cat aca aaa gca gaa cgg aat att ctg gag gaa gta aag cat ccc         486
Ala His Thr Lys Ala Glu Arg Asn Ile Leu Glu Glu Val Lys His Pro
        140                 145                 150 ttc atc gtg gat tta att tat gcc ttt cag act ggt gga aaa ctc tac         534
Phe Ile Val Asp Leu Ile Tyr Ala Phe Gln Thr Gly Gly Lys Leu Tyr
        155                 160                 165 ctc atc ctt gag tat ctc agt gga gga gaa cta ttt atg cag tta gaa         582
Leu Ile Leu Glu Tyr Leu Ser Gly Gly Glu Leu Phe Met Gln Leu Glu
170                 175                 180                 185 aga gag gga ata ttt atg gaa gac act gcc tgc ttt tac ttg gca gaa         630
Arg Glu Gly Ile Phe Met Glu Asp Thr Ala Cys Phe Tyr Leu Ala Glu
                190                 195                 200 atc tcc atg gct ttg ggg cat tta cat caa aag ggg atc atc tac aga         678
Ile Ser Met Ala Leu Gly His Leu His Gln Lys Gly Ile Ile Tyr Arg
            205                 210                 215 gac ctg aag ccg gag aat atc atg ctt aat cac caa ggt cat gtg aaa         726
Asp Leu Lys Pro Glu Asn Ile Met Leu Asn His Gln Gly His Val Lys
        220                 225                 230 cta aca gac ttt gga cta tgc aaa gaa tct att cat gat gga aca gtc         774
Leu Thr Asp Phe Gly Leu Cys Lys Glu Ser Ile His Asp Gly Thr Val
        235                 240                 245 aca cac aca ttt tgt gga aca ata gaa tac atg gcc cct gaa atc ttg         822
Thr His Thr Phe Cys Gly Thr Ile Glu Tyr Met Ala Pro Glu Ile Leu
250                 255                 260                 265 atg aga agt ggc cac aat cgt gct gtg gat tgg tgg agt ttg gga gca         870
Met Arg Ser Gly His Asn Arg Ala Val Asp Trp Trp Ser Leu Gly Ala
                270                 275                 280
```

```
tta atg tat gac atg ctg act gga gca ccc cca ttc act ggg gag aat      918
Leu Met Tyr Asp Met Leu Thr Gly Ala Pro Pro Phe Thr Gly Glu Asn
            285                 290                 295 aga aag aaa aca att gac aaa atc ctc aaa tgt aaa ctc aat ttg cct      966
Arg Lys Lys Thr Ile Asp Lys Ile Leu Lys Cys Lys Leu Asn Leu Pro
        300                 305                 310 ccc tac ctc aca caa gaa gcc aga gat ctg ctt aaa aag ctg ctg aaa     1014
Pro Tyr Leu Thr Gln Glu Ala Arg Asp Leu Leu Lys Lys Leu Leu Lys
        315                 320                 325 aga aat gct gct tct cgt ctg gga gct ggt cct ggg gac gct gga gaa     1062
Arg Asn Ala Ala Ser Arg Leu Gly Ala Gly Pro Gly Asp Ala Gly Glu
330                 335                 340                 345 gtt caa gct cat cca ttc ttt aga cac att aac tgg gaa gaa ctt ctg     1110
Val Gln Ala His Pro Phe Phe Arg His Ile Asn Trp Glu Glu Leu Leu
                350                 355                 360 gct cga aag gtg gag ccc ccc ttt aaa cct ctg ttg caa tct gaa gag     1158
Ala Arg Lys Val Glu Pro Pro Phe Lys Pro Leu Leu Gln Ser Glu Glu
            365                 370                 375 gat gta agt cag ttt gat tcc aag ttt aca cgt cag aca cct gtc gac     1206
Asp Val Ser Gln Phe Asp Ser Lys Phe Thr Arg Gln Thr Pro Val Asp
        380                 385                 390 agc cca gat gac tca act ctc agt gaa agt gcc aat cag gtc ttt ctg     1254
Ser Pro Asp Asp Ser Thr Leu Ser Glu Ser Ala Asn Gln Val Phe Leu
        395                 400                 405 ggt ttt aca tat gtg gct cca tct gta ctt gaa agt gtg aaa gaa aag     1302
Gly Phe Thr Tyr Val Ala Pro Ser Val Leu Glu Ser Val Lys Glu Lys
410                 415                 420                 425 ttt tcc ttt gaa cca aaa atc cga tca cct cga aga ttt att ggc agc     1350
Phe Ser Phe Glu Pro Lys Ile Arg Ser Pro Arg Arg Phe Ile Gly Ser
                430                 435                 440 cca cga aca cct gtc agc cca gtc aaa ttt tct cct ggg gat ttc tgg     1398
Pro Arg Thr Pro Val Ser Pro Val Lys Phe Ser Pro Gly Asp Phe Trp
            445                 450                 455 gga aga ggt gct tcg gcc agc aca gca aat cct cag aca cct gtg gaa     1446
Gly Arg Gly Ala Ser Ala Ser Thr Ala Asn Pro Gln Thr Pro Val Glu
        460                 465                 470 tac cca atg gaa aca agt ggc ata gag cag atg gat gtg aca atg agt     1494
Tyr Pro Met Glu Thr Ser Gly Ile Glu Gln Met Asp Val Thr Met Ser
475                 480                 485 ggg gaa gca tcg gca cca ctt cca ata cga cag ccg aac tct ggg cca     1542
Gly Glu Ala Ser Ala Pro Leu Pro Ile Arg Gln Pro Asn Ser Gly Pro
490                 495                 500                 505 tac aaa aaa caa gct ttt ccc atg atc tcc aaa cgg cca gag cac ctg     1590
Tyr Lys Lys Gln Ala Phe Pro Met Ile Ser Lys Arg Pro Glu His Leu
                510                 515                 520 cgt atg aat cta tgacagagca atgcttttaa tgaatttaag gcaaaaggt         1642
Arg Met Asn Leu
            525 ggagagggag atgtgtgagc atcctgcaag gtgaaacaag actcaaaatg acagtttcag   1702 agagtcaatg tcattacata gaacacttcg gacacaggaa aaataaacgt ggattttaaa   1762 aaatcaatca atggtgcaaa aaaaaactta agcaaaata gtattgctga actcttaggc    1822 acatcaatta attgattcct cgcgacatct ttctcaacct tatcaaggat ttcatgttg    1882 atgactcgaa actgacagta ttaagggtag gatgttgctc tgaatcactg tgagtctgat   1942 gtgtgaagaa gggtatcctt tcattaggca agtacaaatt gcctataata cttgcaacta   2002 aggacaaatt agcatgcaag cttggtcaaa cttttcccag gcaaatggg aaggcaaaga    2062 caaaagaaac ttaccaattg atgttttacg tgcaaacaac ctgaatcttt tttttatata   2122
```

```
aatatatatt tttcaaatag atttttgatt cagctcatta tgaaaaacat cccaaacttt    2182
aaaatgcgaa attattggtt ggtgtgaaga aagccagaca acttctgttt cttctcttgg    2242
tgaaataata aaatgcaaat gaatcattgt taacacagct gtggctcgtt tgagggattg    2302
gggtggacct ggggtttatt ttcagtaacc cagctgcgga gcct                    2346

<210> SEQ ID NO 4
<211> LENGTH: 525
<212> TYPE: PRT
<213> ORGANISM: Homo sapiens
<220> FEATURE:
<223> OTHER INFORMATION: p70(alpha) S6 Kinase protein

<400> SEQUENCE: 4

Met Arg Arg Arg Arg Arg Asp Gly Phe Tyr Pro Ala Pro Asp Phe
 1               5                  10                  15

Arg Asp Arg Glu Ala Glu Asp Met Ala Gly Val Phe Asp Ile Asp Leu
                20                  25                  30

Asp Gln Pro Glu Asp Ala Gly Ser Glu Asp Leu Glu Glu Gly Gly
            35                  40                  45

Gln Leu Asn Glu Ser Met Asp His Gly Val Gly Pro Tyr Glu Leu
        50                  55                  60

Gly Met Glu His Cys Glu Lys Phe Glu Ile Ser Glu Thr Ser Val Asn
 65                 70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
        115                 120                 125

Met Ile Val Arg Asn Ala Lys Asp Thr Ala His Thr Lys Ala Glu Arg
130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
        195                 200                 205

Leu His Gln Lys Gly Ile Ile Tyr Arg Asp Leu Lys Pro Glu Asn Ile
    210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                245                 250                 255

Ile Glu Tyr Met Ala Pro Glu Ile Leu Met Arg Ser Gly His Asn Arg
            260                 265                 270

Ala Val Asp Trp Trp Ser Leu Gly Ala Leu Met Tyr Asp Met Leu Thr
        275                 280                 285

Gly Ala Pro Pro Phe Thr Gly Glu Asn Arg Lys Lys Thr Ile Asp Lys
    290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
                325                 330                 335
```

```
Gly Ala Gly Pro Gly Asp Ala Gly Glu Val Gln Ala His Pro Phe Phe
            340                 345                 350
Arg His Ile Asn Trp Glu Glu Leu Ala Arg Lys Val Glu Pro Pro
            355                 360                 365
Phe Lys Pro Leu Leu Gln Ser Glu Glu Asp Val Ser Gln Phe Asp Ser
370                 375                 380
Lys Phe Thr Arg Gln Thr Pro Val Asp Ser Pro Asp Asp Ser Thr Leu
385                 390                 395                 400
Ser Glu Ser Ala Asn Gln Val Phe Leu Gly Phe Thr Tyr Val Ala Pro
                405                 410                 415
Ser Val Leu Glu Ser Val Lys Glu Lys Phe Ser Phe Glu Pro Lys Ile
            420                 425                 430
Arg Ser Pro Arg Arg Phe Ile Gly Ser Pro Arg Thr Pro Val Ser Pro
            435                 440                 445
Val Lys Phe Ser Pro Gly Asp Phe Trp Gly Arg Gly Ala Ser Ala Ser
            450                 455                 460
Thr Ala Asn Pro Gln Thr Pro Val Glu Tyr Pro Met Glu Thr Ser Gly
465                 470                 475                 480
Ile Glu Gln Met Asp Val Thr Met Ser Gly Glu Ala Ser Ala Pro Leu
                485                 490                 495
Pro Ile Arg Gln Pro Asn Ser Gly Pro Tyr Lys Lys Gln Ala Phe Pro
            500                 505                 510
Met Ile Ser Lys Arg Pro Glu His Leu Arg Met Asn Leu
            515                 520                 525

<210> SEQ ID NO 5
<211> LENGTH: 31
<212> TYPE: PRT
<213> ORGANISM: Homo sapiens
<220> FEATURE:
<223> OTHER INFORMATION: Sequence derived from C-terminus of ribosomal
      S6 protein

<400> SEQUENCE: 5

Lys Glu Ala Lys Glu Lys Arg Gln Glu Gln Ile Ala Arg Arg Arg Leu
1               5                   10                  15
Ser Ser Leu Arg Ala Ser Thr Ser Lys Ser Glu Ser Ser Gln Lys
            20                  25                  30

<210> SEQ ID NO 6
<211> LENGTH: 19
<212> TYPE: PRT
<213> ORGANISM: Homo sapiens
<220> FEATURE:
<223> OTHER INFORMATION: Sequence derived from C-terminus of ribosomal
      S6 protein

<400> SEQUENCE: 6

Arg Arg Arg Leu Ser Ser Leu Arg Ala Ser Thr Ser Lys Ser Glu Ser
1               5                   10                  15
Ser Gln Lys

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      protease target substrate for p70(alpha) S6 Kinase
      isoforms
```

```
<400> SEQUENCE: 7

Lys Lys Arg Asn Arg Thr Leu Ser Val Ala
  1               5                  10

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence:  Synthetic
      protease target substrate for p70(beta) S6 Kinase
      isoforms

<400> SEQUENCE: 8

Arg Arg Leu Ser Ser Leu Arg Ala Ser Thr Ser Lys Ser Glu Ser Ser
  1               5                  10                  15

Gln Lys
```

IDENTIFICATION AND FUNCTIONAL CHARACTERIZATION OF A NOVEL RIBOSOMAL S6 PROTEIN KINASE

This is a divisional application of U.S. application Ser. No. 09/762,258 (filed May 29, 2001) now U.S. Pat. No. 6,830,909 (issued Dec. 14, 2004) which is a U.S. National Phase Application of International Application PCT/US99/17595 (filed Aug. 4, 1999) which claims the benefit of U.S. Provisional Application 60/095,268 (filed Aug. 4, 1998), all of which are herein incorporated by reference in their entirety.

FIELD OF THE INVENTION

The present invention relates to a novel S6 kinase (p70β$^{Sk6}$), mutant variants thereof, methods of making and using this S6 kinase, and related nucleic acids and antibodies. The invention also relates to binding partners of the S6 kinase, methods of identifying the binding partners and antibodies thereto.

BACKGROUND OF THE INVENTION

The 40S ribosomal protein S6 is a component of the 40S subunit of eukaryotic ribosomes. The ribosomes are part of the cellular machinery responsible for translation of mRNA and protein synthesis. The S6 protein is phosphorylated in response to certain cellular signaling events such as hormone or growth factor induced cellular proliferation. p70 S6 kinase (p70$^{S6k}$) is responsible for S6 phosphorylation and is believed to be the major physiological S6 kinase in mammalian cells (Proud, 1996 *Trends Biochem. Sci.* 21: 181-185).

1. p70α S6 Kinase

A. Structure and Function

The first p70 S6 kinase identified was the alpha (α) form. The gene encoding the human p70α S6 kinase (p70$^{S6k}$) was isolated in 1991 (Grove et al., 1991 *Mol. Cell. Biol.* 11: 5541-5550). Other p70α S6 kinase sequences have been described in *Mus musculus* (GenBank Accession No. SEG_AB015196S, AB015197, and AB015196), *Xenopus laevis* (GenBank Accession No. X66179), and rat (GenBank Accession No. M57428).

Two p70α S6 kinase isoforms were identified: p70α-I (GenBank Accession No. M60724) and p70α-II (GenBank Accession No. M60725). The two p70α S6 kinase isoforms differ only in their amino termini by 23 amino acid residues resulting in a 70 kD protein and a 85 kD protein. The isoforms are referred to in the literature as p70$^{S6k}$/p85$^{S6k}$ or p70α S6 kinase. Both isoforms share similar activity towards ribosomal protein S6 in vitro but are expressed in different cells and tissues. The two isoforms are produced by two mRNA products and are not a result of post-translational modifications. They are serine/threonine kinases and are known to act on the substrate KKRNRTLSVA (SEQ ID No. 7) (Pai et al., 1994 *Eur. J. Immunol.* 24: 2364-8; and Leighton et al., 1995 *FEBS Letters* 375: 289-93).

The p70α S6 kinase plays an important role in the progression of cells from G1 to S phase of the cell cycle and in the initiation of protein synthesis. Recently, p70α S6 kinase has been demonstrated to regulate the translation of a class of mRNAs containing an oligopyrimidine tract in their 5' untranslated region. This class of mRNAs, termed 5'TOP mRNAs, represent up to 20% of a cell's total mRNA. Many of the proteins encoded by 5'TOP mRNAs are translational apparatus proteins and cell-cycle progression proteins.

The p70α S6 kinase has four identified interdependent domains: (1) a catalytic domain, (2) a kinase extension domain, (3) a pseudosubstrate autoinhibitory domain, and (4) the N-terminal domain. The catalytic domain is located in the middle of the protein and is followed by the kinase extension domain, which is a unique feature for the PKA family. The pseudosubstrate autoinhibitory domain is also unique for the p70α S6 kinase, not having been observed in any other known kinases. It possesses 5 phosphorylation sites which are responsible for the p70α S6 kinase regulation. The N-terminal domain mediates the sensitivity for rapamycin, which strongly inhibits serum-induced phosphorylation and activation of the p70α S6 kinase. This domain may also mediate the interaction with a yet unknown phosphatase.

B. Regulators and Cascades

Growth factors, such as insulin, and mitogens are known to activate in vivo p70α S6 kinase (Alessi et al., 1998 *Curr. Biol.* 8: 69-81). Heat shock also activates p70α S6 kinase (Lin et al., 1997 *J. Biol. Chem.* 272: 31196-31202). Certain drugs have been identified that regulate p70α S6 kinase activity including: rapamycin, wortmannin, Ro31-8220, GF109203X, LY294002, phenylephrine (PE), PD098059, SQ20006, polymerized collagen, forskolin, interleukin-10 (IL-10), demethoxyviridin, phorbol 12-myristate 13-acetate (PMA), A23187, bombesin and antibodies which recognize the p70α S6 kinase (Proud, 1996; Morreale et al., 1997 *FEBS Letters* 417: 38-42; Kanda et al., 1997 *J. Biol. Chem.* 272: 23347-23353; Boluyt et al., 1997 *Circ. Res.* 81: 176-186; Coolican et al., 1997 *J. Biol. Chem.* 272: 6653-6662; Koyama et al., 1996 *Cell* 87: 1069-1078; Busca et al., 1996 *J. Biol. Chem.* 271: 31824-31830; Crawley et al., 1996 *J. Biol. Chem.* 271: 16357-16362; and Petritsch et al., 1995 *Eur. J. Biochem.* 230: 431-8). The immunosuppressant rapamycin (Rap) is the most potent inhibitor of p70α S6 kinase described (Pullen et al., 1997 *FEBS Letters* 410: 78-82).

p70α S6 kinase is an enzyme which lies downstream of phosphoinositide 3-kinases (PI3-kinase). The mechanisms regulating the p70α S6 kinase have not been fully elucidated. PI3-kinase has recently been shown to activate another phosphoinositide-dependent protein kinase, termed PDK-1. So far, only PDK-1 has been shown to phosphorylate p70α S6 kinase in vivo, and this phosphorylation is essential for p70β$^{S6k}$ activity towards ribosomal S6 protein. Wortmannin, a fungal inhibitor which down-regulates the p70α S6 kinase, is believed to act by inhibiting PI-3 kinase. In contrast, another fungal inhibitor, rapamycin, inhibits the p70α S6 kinase by another cascade pathway involving the mammalian target of rapamycin (mTOR; also known as RAFT or FRAP) (Proud, 1996; Stewart et al., 1994 *BioEssays* 16: 809-815). mTOR is a member of the PIK-related family of protein kinases (Pullen et al., 1997). Additional regulators of the p70β S6 kinase include, but are not limited to protein kinase B (PKB), Cdc42, and 'Rac. The role of most of these proteins as p70α S6 kinase regulators has yet to be fully elucidated.

SUMMARY OF THE INVENTION

The present invention is based on our discovery of a new gene which encodes a novel S6 kinase (p70β$^{S6k}$). The invention includes isolated nucleic acid molecules selected from the group consisting of an isolated nucleic acid molecule that encodes the amino acid sequence of SEQ ID No. 2, (e.g., SEQ ID No. 1) an isolated nucleic acid molecule that encodes a fragment of SEQ ID No. 2, an isolated nucleic acid molecule which hybridizes to the complement of a nucleic acid molecule comprising SEQ ID No. 1 under conditions of sufficient stringency to produce a clear signal and an isolated nucleic acid molecule which hybridizes to the complement of a nucleic acid molecule that encodes the amino acid sequence of SEQ ID No. 2 under conditions of sufficient stringency to produce a clear signal.

The present invention further includes the nucleic acid molecules operably linked to one or more expression control elements, including vectors comprising the isolated nucleic acid molecules. The invention further includes host cells transformed to contain the nucleic acid molecules of the invention and methods for producing a protein comprising the step of culturing a host cell transformed with the nucleic acid molecule of the invention under conditions in which the protein is expressed.

The invention further provides an isolated polypeptide selected from the group consisting of an isolated polypeptide comprising the amino acid sequence of SEQ ID No. 2, an isolated polypeptide comprising a fragment of SEQ ID No. 2, an isolated polypeptide comprising conservative amino acid substitutions of SEQ ID No. 2 and naturally occurring amino acid sequence variants of SEQ D No. 2.

The invention further provides an isolated antibody that binds to a polypeptide of the invention, including monoclonal and polyclonal antibodies and fragments thereof.

The invention further provides methods of identifying an agent which modulates the expression of a nucleic acid encoding the protein having the sequence of SEQ ID No. 2 comprising the steps of: exposing cells which express the nucleic acid to the agent; and determining whether the agent modulates expression of said nucleic acid, thereby identifying an agent which modulates the expression of a nucleic acid encoding the protein having the sequence of SEQ ID No. 2.

The invention further provides methods of identifying an agent which modulates at least one activity of a protein comprising the sequence of SEQ ID No. 2 comprising the steps of: exposing cells which express the protein to the agent; and determining whether the agent modulates at least on activity of said protein, thereby identifying an agent which modulates at least one activity of a protein comprising the sequence of SEQ ID No. 2.

The invention further provides methods of identifying binding partners for a protein comprising the sequence of SEQ ID No. 2 or activated variants thereof, comprising for example, the steps of: exposing said protein to a potential binding partner; and determining if the potential binding partner binds to said protein, thereby identifying binding partners for a protein comprising the sequence of SEQ ID No. 2. Exposing may be accomplished by expressing the protein in a cell.

The present invention further provides methods of modulating the expression of a nucleic acid encoding the protein having the sequence of SEQ ID No. 2 comprising the step of: administering an effective amount of an agent which modulates the expression of a nucleic acid encoding the protein having the sequence of SEQ ID No. 2. The invention also provides methods of modulating at least one activity of a protein comprising the sequence of SEQ ID No. 2 comprising the step of: administering an effective amount of an agent which modulates at least one activity of a protein comprising the sequence of SEQ ID No. 2.

BRIEF DESCRIPTION OF THE DRAWINGS

FIG. 1. Nucleic acid sequence of p70β$^{S6k}$ (SEQ D No. 1) and comparison with p70α$^{S6k}$ (SEQ ID No. 3). Sequence analysis of cDNA encoding the p70β S6 kinase. p70β cDNA may encode two isoforms with the use of alternative start codon. The longer form may encode a protein of 495 amino acid residues and the shorter form, 482 amino acids (aa). Alternative start codons and a stop codon are highlighted.

FIG. 2A-2B. Amino Acid Sequence of p70β$^{S6k}$ (SEQ ID No. 2) and comparison with p70α$^{S6K}$ (SEQ ID No. 4).

FIG. 2A. Alignment of predicted protein sequences corresponding to the p70α$^{S6K}$ and p70β S6 kinases. Identical amino acids are boxed.

FIG. 2B. Comparative analysis of regulatory domains and phosphorylation sites between p70α and β S6 kinases.

FIG. 3A. Nylon membrane containing 2 μg of gel-separated, pre-bound poly(A)+ RNA samples from various human tissues was hybridized with cDNA fragments of p70α$^{S6k}$, p70β$^{S6k}$ or β-actin labeled by random priming. The upper, middle and lower panels are autoradiographs probed with p70β$^{S6k}$, p70α$^{S6k}$ and β-actin, respectively. Each lane contains mRNA prepared from: heart (lane 1), brain (lane 2), placenta (lane 3), lung (lane 4), liver (lane 5), skeletal muscle (lane 6), kidney (lane 7), pancreas (lane 8), spleen (lane 9), thymus (lane 10), prostate (lane 11), testis (lane 12), ovary (lane 13), small intestine (lane 14), mucosal lining of the colon (lane 15), and peripheral blood leukocytes (lane 16).

FIG. 3B. Nylon membrane containing 2 μg of mRNA isolated from tumor ell lines was probed with the 3' cDNA fragment from p70β$^{S6k}$, which was labeled by random-prime labeling. Specific binding was determined by autoradiography. Promyelocytic leukemia HL-60 (lane 1), HeLa cell S3 (lane 2, chronic myelogenous leukemia K562 (lane 3), lymphoblastic leukemia MOLT-4 (lane 4), Burkitt's lymphoma Raji (lane 5), colorectal adenocarcinoma SW480 (lane 6), lung carcinoma (lane 7), and melanoma G361 (lane 8).

FIG. 4A-4B. Phosphorylation of the ribosomal protein S6 (FIG. 4A) and its C-terminal synthetic peptide (FIG. 4B) by p70α$^{S6k}$ and p70β$^{S6k}$. Ribosomal S6 protein (purified ribosomal 40S subunits from liver) and synthetic peptides corresponding to the S6 protein C-terminus (e.g., KEAKEKRQE-QIARRRLSSLRASTSKSESSQK-long form (SEQ ID No. 5) and RRRLSSLRASTSKSESSQK-(SEQ ID No. 6) short form) were used to measure the activity of the p70α$^{S6k}$ and p70β$^{S6k}$. HEK293 cells were transfected with plasmids containing Flag-tag or EE-tag versions of p70α$^{S6k}$ or p70β$^{S6k}$. Recombinant proteins were immunoprecipitated with anti-EE or anti-Flag antibodies and an in vitro kinase reaction performed in the presence of the ribosomal 40S subunits or synthetic peptides. After SDS-PAGE analysis, phosphorylation of the S6 protein and synthetic peptides was measured by PhosphoImager and expressed in arbitrary units (PI units).

FIG. 5A-5B. Stimulation of p70β$^{S6k}$ Activity by insulin, serum and TPA.

FIG. 5A. CHO-IR cells were transfected with mock (lane 1) or plasmids containing cDNAs of FLAG-tagged p70α-I (lanes 2 and 3) or FLAG-tagged p70β-II (lanes 4 to 7). After serum starvation for 16 hrs, cells were treated with the vehicle (lanes 2 and 4), $10^{-7}$ M insulin for 10 min (lanes 3 and 5), 15% serum for 10 min (lane 6) or 500 nM TPA for 30 min (lane 7). After cell lysis and subsequent immunoprecipitation with anti-FLAG antibodies, immunoprecipitates were subjected to a p70 S6 kinase assay using 40S subunits as substrates. The reaction mixture was separated by SDS-PAGE, transferred onto PVDF membrane. The membrane was analyzed by autoradiography (upper panel) and then immunoblotted with anti-FLAG antibodies (lower panel). A representative of three experiments is shown. $^{32}$P incorporation into S6 was quantified by Molecular Dynamics. PhosphorImager™ and is expressed in arbitrary units (PI units).

FIG. 5B. Stimulation of the p70α$^{S6k}$ and p70β$^{S6k}$ activity towards ribosomal S6 protein by PDGF in PAE-PDGF-R cells. PAE-PDGF-R cells were transfected with EE-tagged p70α$^{S6k}$ and p70β$^{S6k}$ plasmids using lipofectAMINE. After 24 hr, transfected cells were serum-starved for 16 hr and stimulated with 20 ng/ml PDGF BB (Calbiochem) for 20 min. Control cells were treated with the vehicle under the same conditions. After immunoprecipitation with anti-EE antibodies, an in vitro kinase reaction was carried out in the presence of 40S subunits, containing the S6 protein. Reaction mixtures were separated by SDS-PAGE and incorporation of $^{32}$P into S6 protein was measured by PhosphoImager.

FIG. 6A-6B. Effects of rapamycin and wortmannin on p70β$^{S6k}$ and p70α$^{S6k}$. Effects of rapamycin and wortmannin on S6 phosphorylation activity of p70α-I or p70β-II. HEK293 cells were transfected with mock cDNA or plasmids containing FLAG-tagged p70β1 or p70β2 isoforms. After 48 h of transfection, cells were treated with vehicle or indicated concentrations of rapamycin or wortmannin for 30 min. After immunoprecipitation with anti-FLAG antibodies, the kinase activity was determined by a p70 S6 kinase assay using 40S subunits as substrates. The proteins of the reaction mixture were separated by SDS-PAGE, transferred onto PVDF membrane and analyzed by autoradiography (FIGS. 6A and 6B, upper panels). Subsequent immunoblotting with anti-FLAG antibody confirmed the expression of p70α-I (FIG. 6A, lower panel) and p70β-II (FIG. 6B, lower panel). A representative of three experiments is shown. $^{32}$P incorporation into S6 was quantified by PhosphorImager and is expressed in arbitrary units (PI units).

FIG. 12: p70α$^{S6k}$ (T412D) activity. Activity of p70α$^{S6k}$ (T412D) variant as compared to wt p70α$^{S6k}$ under S6 Kinase and autophosphorylation assays.

DETAILED DESCRIPTION OF THE PREFERRED EMBODIMENT

Figure 2B:
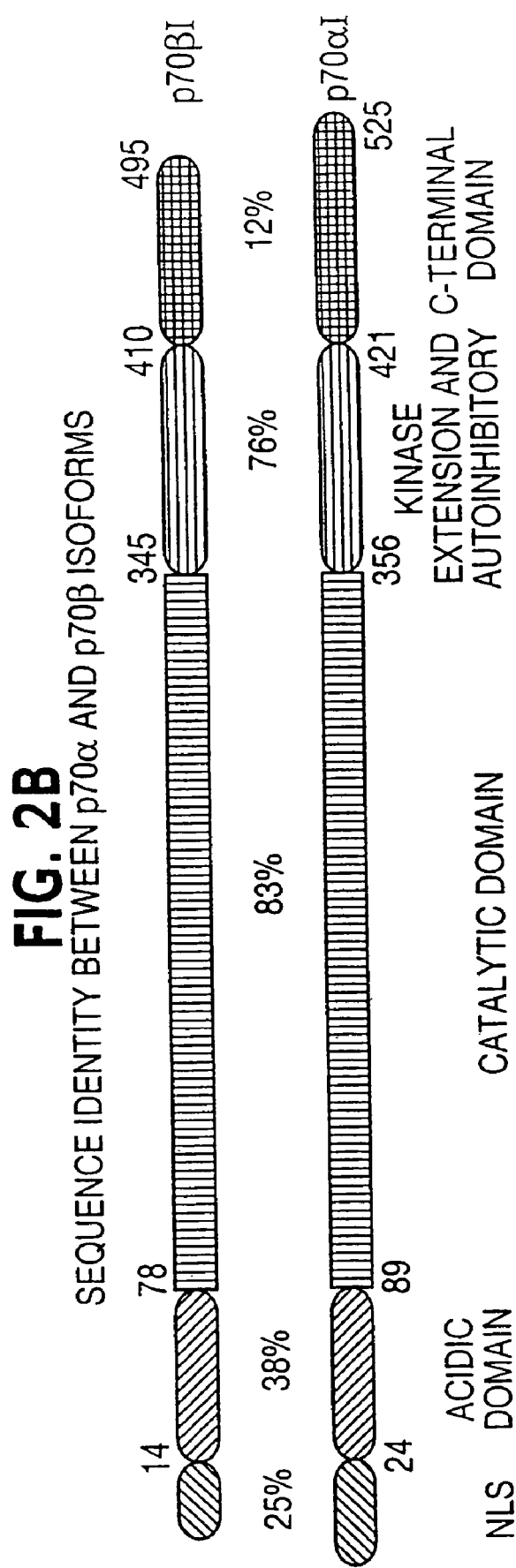

The terms "p70α", "p70α$^{S6k}$" and "p70α$^{S6}$ kinase" are meant to include the two isoforms, p70 and p85, both of which phosphorylate the ribosomal protein S6. By "p70α-1" and "p70α-I" are meant the p85 isoform of the p70α$^{S6}$ kinase. By "p70α-2" and "p70α-II" are meant the p70 isoform of the p70α$^{S6}$ kinase.

The terms "p70β", "p70β$^{S6k}$" and "p70β$^{S6}$ kinase" include the newly identified S6 kinase and all its isoforms.

I. General Description

The present invention is based in part on identifying a new gene that encodes a novel S6 kinase (p70β$^{S6k}$). This new gene and the protein that it encodes are members of the family of S6 kinases, of which the p70α-I and -II (also referred to as p70α-1 and p70α-2) isoforms have already been reported.

The protein can serve as a target for agents that can be used to modulate the expression or activity of the protein. For example, agents may be identified which modulate biological processes associated with ribosomal activity.

The present invention is further based on the development of methods for isolating binding partners that bind to the protein or its activated variants. Probes based on the protein are used as capture probes to isolate potential binding partners, such as other proteins. Dominant negative proteins, DNAs encoding these proteins, antibodies to these proteins, peptide fragments of these proteins or mimics of these proteins may be introduced into cells to affect function. Additionally, these proteins provide a novel target for screening of synthetic small molecules and combinatorial or naturally occurring compound libraries to discover novel therapeutics to regulate ribosomal function.

II. Specific Embodiments

A. The Ribosome Associated Protein

The present invention provides isolated protein, allelic variants of the protein, and conservative amino acid substitutions of the protein, including substitutions that activate the protein. As used herein, the protein or polypeptide refers to a protein that has the human amino acid sequence of depicted in SEQ ID No. 2. The invention includes naturally occurring allelic variants and proteins that have a slightly different amino acid sequence than that specifically recited above. Allelic variants, though possessing a slightly different amino acid sequence than those recited above, will still have the same or similar biological functions associated with the disclosed protein.

As used herein, the family of proteins related to the disclosed protein refer to proteins that have been isolated from organisms in addition to humans. The methods used to identify and isolate other members of the family of proteins related to the disclosed protein are described below.

The proteins of the present invention are preferably in isolated form. As used herein, a protein is said to be isolated when physical, mechanical or chemical methods are employed to remove the protein from cellular constituents that are normally associated with the protein. A skilled artisan can readily employ standard purification methods to obtain an isolated protein.

The proteins of the present invention further include conservative variants of the proteins herein described. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein can be altered without adversely affecting a biological activity. Accordingly, the amino acid sequence can be altered, for example to render the peptide more hydrophobic or hydrophilic, without adversely affecting the biological activities of the protein. Conservative substitutions may irreversibly activate the protein.

Ordinarily, the allelic variants, the conservative substitution variants, the members of the protein family, will have an amino acid sequence having at least 71%-about 75% amino acid sequence identity with the human sequence set forth in SEQ ID No. 2, more preferably at least 80%, even more preferably at least 90%, and most preferably at least 95%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Homology or identity is determined by BLAST (Basic Local Alignment Search Tool) analysis using the algorithm employed by the programs blastp, blastn, blastx, tblastn and tblastx (Karlin, et al. Proc. Natl. Acad. Sci. USA 87: 2264-2268 (1990) and Altschul, S. F. J. Mol. Evol. 36: 290-300 (1993), fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (Nature Genetics 6: 119-129 (1994)) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff, et al. Proc. Natl. Acad. Sci. USA 89: 10915-10919 (1992), fully incorporated by reference). For blastn, the scoring matrix is set by the ratios of M (i.e., the reward score for a pair of matching residues) to N USA 87: 2264-2268 (1990) and (i.e., the penalty score for mismatching residues), wherein the default values for M and N are 5 and −4, respectively.

Thus, the proteins of the present invention include molecules having the amino acid sequence disclosed in SEQ ID No. 2; fragments thereof having a consecutive sequence of at least about 3, 5, 10 or 15 amino acid residues of the disclosed protein; amino acid sequence variants of such sequence wherein an amino acid residue has been inserted N- or C-terminal to, or within, the disclosed sequence; amino acid sequence variants of the disclosed sequence, or their fragments as defined above, that have been substituted by another residue. Contemplated variants further include those containing predetermined mutations by, e.g., homologous recombination, site-directed or PCR mutagenesis, and the corresponding proteins of other animal species, including but not limited to rabbit, rat, murine, porcine, bovine, ovine, equine and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope). Proteins of the invention may include fusion proteins comprising any of the foregoing.

As described below, members of the family of proteins can be used: 1) to identify agents which modulate at least one activity of the protein, including agents which may modulate phosphorylation mediated by the protein; 2) in methods of identifying binding partners for the protein, 3) as an antigen to raise polyclonal or monoclonal antibodies, and 4) as a therapeutic agent.

B. Nucleic Acid Molecules

The present invention further provides nucleic acid molecules that encode the protein having SEQ ID No. 2 and the related proteins herein described, preferably in isolated form. As used herein, "nucleic acid" is defined as RNA or DNA that encodes a peptide as defined above, or is complementary to nucleic acid sequence encoding such peptides, or hybridizes to such nucleic acid and remains stably bound to it under appropriate stringency conditions, or encodes a polypeptide sharing at least 75% sequence identity, preferably at least 80%, and more preferably at least 85%, with the peptide sequences. Specifically contemplated are genomic DNA, cDNA, mRNA and antisense molecules, as well as nucleic acids based on alternative backbone or including alternative bases whether derived from natural sources or synthesized. Such hybridizing or complementary nucleic acids, however, are defined further as being novel and nonobvious over any prior art nucleic acid including that which encodes, hybridizes under appropriate stringency conditions, or is complementary to nucleic acid encoding a protein according to the present invention.

"Stringent conditions" are those that (1) employ low ionic strength and high temperature for washing, for example, 0.015 M NaCl, 0.0015 M sodium titrate, 0.1% SDS at 50° C.; or (2) employ during hybridization a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

As used herein, a nucleic acid molecule is said to be "isolated" when the nucleic acid molecule is substantially separated from contaminant nucleic acid encoding other polypeptides from the source of nucleic acid.

The present invention further provides fragments of the encoding nucleic acid molecule. As used herein, a fragment of an encoding nucleic acid molecule refers to a small portion of the entire protein encoding sequence. The size of the fragment will be determined by the intended use. For example, if the fragment is chosen so as to encode an active portion of the protein, the fragment will need to be large enough to encode the functional region(s) of the protein. If the fragment is to be used as a nucleic acid probe or PCR primer, then the fragment length is chosen so as to obtain a relatively small number of false positives during probing/priming.

Fragments of the encoding nucleic acid molecules of the present invention (i.e., synthetic oligonucleotides) that are used as probes or specific primers for the polymerase chain reaction (PCR), or to synthesize gene sequences encoding proteins of the invention can easily be synthesized by chemical techniques, for example, the phosphotriester method of Matteucci, et al., (*J. Am. Chem. Soc.* 103: 3185-3191, 1981) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art known labels to obtain a labeled encoding nucleic acid molecule.

Modifications to the primary structure itself by deletion, addition, or alteration of the amino acids incorporated into the protein sequence during translation can be made without destroying the activity of the protein. Such substitutions or other alterations result in proteins having an amino acid sequence encoded by a nucleic acid falling within the contemplated scope of the present invention.

C. Isolation of Other Related Nucleic Acid Molecules

As described above, the identification of the human nucleic acid molecule having SEQ ID No. 1 allows a skilled artisan to isolate nucleic acid molecules that encode other members of the p70$\beta^{S6k}$ family in addition to the human sequence herein described. Further, the presently disclosed nucleic acid molecules allow a skilled artisan to isolate nucleic acid molecules that encode other members of the p70$\beta^{S6k}$ family of proteins in addition to the disclosed protein having SEQ ID No. 2.

Essentially, a skilled artisan can readily use the amino acid sequence of SEQ ID No. 2 to generate antibody probes to screen expression libraries prepared from appropriate cells. Typically, polyclonal antiserum from mammals such as rabbits immunized with the purified protein (as described below) or monoclonal antibodies can be used to probe a mammalian cDNA or genomic expression library, such as λgt11 library, to obtain the appropriate coding sequence for other members of the protein family. The cloned cDNA sequence can be expressed as a fusion protein, expressed directly using its own control sequences, or expressed by constructions using control sequences appropriate to the particular host used for expression of the enzyme.

Alternatively, a portion of the coding sequence herein described can be synthesized and used as a probe to retrieve DNA encoding a member of the protein family from any mammalian organism. Oligomers containing approximately 18-20 or 21 nucleotides (encoding about a 67 amino acid stretch) are prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively clone an encoding nucleic acid molecule. A PCR denature/anneal/extend cycle for using such PCR primers is well known in the art and can readily be adapted for use in isolating other encoding nucleic acid molecules.

D. rDNA molecules Containing a Nucleic Acid Molecule

The present invention further provides recombinant DNA molecules (rDNAs) that contain a coding sequence. As used herein, a rDNA molecule is a DNA molecule that has been subjected to molecular manipulation in situ. Methods for generating rDNA molecules are well known in the art, for example, see Sambrook et al., (1989). In the preferred rDNA molecules, a coding DNA sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), pPL and pKK223 available from Pharmacia, Piscataway, N.J.

Expression vectors compatible with eukaryotic cells, preferably those compatible with vertebrate cells, can also be used to form a rDNA molecules the contains a coding sequence. Eukaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene (Southern et al., *J. Mol. Anal. Genet.* 1: 327-341, 1982). Alternatively, the selectable marker can be present on a separate plasmid, and the two vectors are introduced by co-transfection of the host cell, and selected by culturing in the appropriate drug for the selectable marker.

E. Host Cells Containing an Exogenously Supplied Coding Nucleic Acid Molecule

The present invention further provides host cells transformed with a nucleic acid molecule that encodes a protein of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eukaryotic tissue culture cell lines.

Any prokaryotic host can be used to express a rDNA molecule encoding a protein of the invention. The preferred prokaryotic host is E. coli.

Transformation of appropriate cell hosts with a rDNA molecule of the present invention is accomplished by well known methods that typically depend on the type of vector used and host system employed With regard to transformation of prokaryotic host cells, electroporation and salt treatment methods are typically employed, see, for example, Cohen et al., *Proc. Natl. Acad. Sci. USA* 69: 2110, 1972; and Maniatis et al., MOLECULAR CLONING, A LABORATORY MANUAL, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol.* 52: 456, 1973; Wigler et al., *Proc. Natl. Acad. Sci. USA* 76: 1373-76, 1979.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, *J. Mol. Biol.* 98:503, 1975, or Berent et al., *Biotech* 3: 208, 1985 or the proteins produced from the cell assayed via an immunological method.

Recombinant p70$\beta^{S6k}$ DNA can also be utilized to analyze the function of coding and noncoding sequences. For example, the 5' untranslated region of the p70$\beta^{S6k}$ clone contains a GA repeat (nucleotides 1-66 of P70$\beta^{S6k}$), that may modulate the initiation of translation of its mRNA. This sequence can be utilized in an affinity matrix system to purify proteins obtained from cell lysates that associate with the p70$\beta^{S6k}$ GA sequence. Synthetic oligonucleotides would be coupled to the beads and probed with the lysates, as is commonly known in the art. Associated proteins could then be separated using, for example, a two dimensional SDS-PAGE system. Proteins thus isolated could be further identified using mass spectroscopy or protein sequencing.

F. Production of Recombinant Proteins Using a rDNA Molecule

The present invention further provides methods for producing a protein of the invention using nucleic acid molecules herein described. In general terms, the production of a recombinant form of a protein typically involves the following steps:

First, a nucleic acid molecule is obtained that encodes a protein of the invention, such as the nucleic acid molecule depicted in SEQ ID No. 1, or particularly for the p70$\beta^{S6k}$ nucleotides encoding the proline rich domain or the amino terminus of p70$\beta^{S6k}$. The coding sequence is directly suitable for expression in any host, as it is not interrupted by introns. The sequence can be transfected into host cells such as eukaryotic cells or prokaryotic cells. Eukaryotic hosts include mammalian cells (e.g. HEK293 cells, CHO cells and PAE-PDGF-R cells) as well as insect cells such as Sf9 cells using recombinant baculovirus. Alternatively, fragments encoding only portion of p70$\beta^{S6k}$ can be expressed alone or in the form of a fusion protein. For example, the C-terminal fragment of p70$\beta^{S6k}$ containing the proline-rich domain, was expressed in bacteria as a GST- or His-tag fusion protein. These fusion proteins were then purified and used to generate polyclonal antibodies.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

G. In Vitro Methods to Identify Binding Partners

Another embodiment of the present invention provides methods for use in isolating and identifying binding partners of proteins of the invention In detail, a protein of the invention is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner that bound to the protein of the invention can then be removed and further analyzed. To identify and isolate a binding partner, the entire protein, for instance the entire disclosed protein of SEQ ID No. 2 can be used. Alternatively, a fragment of the protein can be used.

As used herein, a cellular extract refers to a preparation or fraction which is made from a lysed or disrupted cell.

A variety of methods can be used to obtain cell extracts. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the protein of the invention under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density/sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the protein of the invention can be immobilized on a solid support. For example, the protein can be attached to a nitrocellulose matrix or acrylic beads. Attachment of the protein to a solid support aids in separating peptide/binding partner pairs from other constituents found in the extract. The identified binding partners can be either a single protein or a complex made up of two or more proteins.

Alternatively, the nucleic acid molecules of the invention can be used in a yeast two-hybrid system. The yeast two-hybrid system has been used to identify other protein partner pairs and can readily be adapted to employ the nucleic acid molecules herein described.

One preferred in vitro binding assay for $p70\beta^{S6k}$ would comprise a mixture of a polypeptide comprising at least the kinase domain of $p70\beta^{S6k}$ and one or more candidate binding targets or substrates. After incubating the mixture under appropriate conditions, one would determine whether $p70\beta^{S6k}$ or a polypeptide fragment thereof containing the kinase region either bound with the candidate substrate or phosphorylated the candidate substrate. For cell-free binding assays, one of the components usually comprises or is coupled to a label. The label may provide for direct detection, such as radioactivity, luminescence, optical or electron density, etc., or indirect detection such as an epitope tag, an enzyme, etc. A variety of methods may be employed to detect the label depending on the nature of the label and other assay components. For example, the label may be detected bound to the solid substrate or a portion of the bound complex containing the label may be separated from the solid substrate, and the label thereafter detected.

H. Methods to Identify Agents that Modulate the Expression a Nucleic Acid Encoding the S6 Kinase Protein.

Another embodiment of the present invention provides methods for identifying agents that modulate the expression of a nucleic acid encoding a protein of the invention such as a protein having the amino acid sequence of SEQ ID No. 2. Such assays may utilize any available means of monitoring for changes in the expression level of the nucleic acids of the invention. As used herein, an agent is said to modulate the expression of a nucleic acid of the invention, for instance a nucleic acid encoding the protein having the sequence of SEQ ID No. 2, if it is capable of up- or down-regulating expression of the nucleic acid in a cell.

In one assay format, cell lines that contain reporter gene fusions between the open reading frame defined by $p70\beta^{S6k}$ nucleotides 77-1,564 or 116-1,564 of SEQ ID No. 1 and any assayable fusion partner may be prepared. Numerous assayable fusion partners are known and readily available including the firefly luciferase gene and the gene encoding chloramphenicol acetyltransferase (Alam et al., 1990 *Anal. Biochem.* 188: 245-254). Cell lines containing the reporter gene fusions are then exposed to the agent to be tested under appropriate conditions and time. Differential expression of the reporter gene between samples exposed to the agent and control samples identifies agents which modulate the expression of a nucleic acid encoding the protein having the sequence of SEQ ID No. 2.

Additional assay formats may be used to monitor the ability of the agent to modulate the expression of a nucleic acid encoding a protein of the invention such as the protein having SEQ ID No. 2. For instance, mRNA expression may be monitored directly by hybridization to the nucleic acids of the invention. Cell lines are exposed to the agent to be tested under appropriate conditions and time and total RNA or mRNA is isolated by standard procedures such those disclosed in Sambrook et al. (MOLECULAR CLONING: A LABORATORY MANUAL, 2nd Ed. Cold Spring Harbor Laboratory Press, 1989).

Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Probes may be designed from the nucleic acids of the invention through methods known in the art. For instance, the G+C content of the probe and the probe length can affect probe binding to its target sequence. Methods to optimize probe specificity are commonly available in Sambrook et al. (1989) or Ausubel et al. (CURRENT PROTOCOLS IN MOLECULAR BIOLOGY, Greene Publishing Co., NY, 1995).

Hybridization conditions are modified using known methods, such as those described by Sambrook et al. (1989) and Ausubel et al. (1995) as required for each probe. Hybridization of total cellular RNA or RNA enriched for polyA RNA can be accomplished in any available format. For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a porous glass wafer. The glass wafer can then be exposed to total cellular RNA or polyA RNA from a sample under conditions in which the affixed sequences will specifically hybridize. Such glass wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up or down regulate the expression of a nucleic acid encoding the protein having the sequence of SEQ ID No. 2 are identified.

I. Cell-Based Methods to Identify Binding Partners and Agents that Modulate at Least One Activity of the S6 Kinase Protein and Related Antibodies.

Another embodiment of the present invention provides methods for identifying agents that modulate at least one activity of a protein of the invention such as the protein having the amino acid sequence of SEQ ID No. 2. Such methods or assays may utilize any means of monitoring or detecting the desired activity.

In one format, the relative amounts of a protein of the invention between a cell population that has been exposed to the agent to be tested compared to an un-exposed control cell population may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

For example, N- and C-terminal fragments of $p70\beta^{S6k}$ can be expressed in bacteria and used to search for proteins which bind to these fragments. Fusion proteins, such as His-tag or GST fusion to the N- or C-terminal regions of $p70\beta^{S6k}$ can be prepared for use as a $p70\beta^{S6k}$ fragment substrate. These fusion proteins can be coupled to Talon or Glutathione-Sepharose beads and then probed with cell lysates. Prior to lysis, the cells may be treated with rapamycin or other drugs which may modulate $p70\beta^{S6k}$ or proteins that interact with $p70\beta^{S6k}$. Lysate proteins binding to the fusion proteins can be resolved by SDS-PAGE, isolated and identified by protein sequencing or mass spectroscopy, as is known in the art. It is likely that signaling molecules containing one or more SH3 domains may bind directly to the C-terminal region of $p70\beta^{S6k}$. The N-terminal domain may have a $p70\beta^{S6k}$-specific phosphatase as a binding partner.

Antibody probes are prepared by immunizing suitable mammalian hosts in appropriate immunization protocols using the peptides, polypeptides or proteins of the invention, such as $p70\beta^{S6k}$, variants and isolated binding partners, if they are of sufficient length, or, if desired, or if required to enhance immunogenicity, conjugated to suitable carriers. Methods for preparing immunogenic conjugates with carriers such as bovine serum albumin (BSA), keyhole limpet hemocyanin (KLH), or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at either the amino or carboxy terminus with a Cys residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

Anti-peptide antibodies can be generated using synthetic peptides corresponding to, for example, the carboxy terminal 15 amino acids $p70\beta^{S6k}$. Synthetic peptides can be as small as 1-3 amino acids in length, but are preferably at least 4 or more amino acid residues long. The peptides are coupled to KLH using standard methods and can be immunized into animals such as rabbits. Polyclonal anti-$p70\beta^{S6k}$ peptide antibodies can then be purified, for example using Actigel beads containing the covalently bound peptide.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in ascites fluid. Of particular interest, are monoclonal antibodies which recognize the proline-rich domain of $p70\beta^{S6k}$.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as Fav, $_{sc}$Fab, Fab', or F(ab')$_2$ fragments is often preferable, especially in a therapeutic context, as these fragments are generally less immunogenic than the whole immunoglobulin. Antibodies may preferably also be human, humanized or chimeric variants of the foregoing. Such antibodies can be less immunogenic when administered to a subject. Methods of producing humanized or chimeric antibodies are well known in the art. The antibodies contemplated also include different isotypes and isotype subclasses (e.g. IgG$_1$, IgG$_2$, IgM, to name a few). These antibodies can be prepared by raising them in vertebrates, in hybridoma cell lines or other cell lines, or by recombinant means. For references on how to prepare these antibodies, see E. Harlow and D. Lane, ANTIBODIES: A LABORATORY MANUAL (Cold Spring Harbor Press, Cold Spring Harbor, N.Y., 1988); Kohler and Milstein, (1976) E. J. Immunol. 6:511; Queen et al. U.S. Pat. No. 5,585,089; and Riechmann et al., Nature 332:323 (1988).

The antibodies or fragments may also be produced, using current technology, by recombinant means. Regions that bind specifically to the desired regions of receptor can also be produced in the context of chimeras with multiple species origin.

In an alternative format, a specific activity of a protein of the invention may be assayed, such as the ability of the protein to phosphorylate a substrate such as polypeptides of the S6 protein. For example, $p70\beta^{S6k}$ has been demonstrated to phosphorylate the S6 protein and a synthetic peptide, RRLSSLRASTSKSESSQK (SEQ ID No. 8). The sequence comprising the synthetic peptide is located in the C-terminus of the S6 protein and is known to contain the five phosphorylation sites targeted by $p70\alpha^{S6k}$ Cell lines or populations are exposed under appropriate conditions to the agent to be tested. Agents which modulate the kinase activity of the protein of the invention are identified by assaying the kinase activity of the protein from the exposed cell line or population and a control, unexposed cell line or population, thereby identifying agents which modulate the kinase activity of the protein. Polypeptides of the S6 protein, such as the above examples, are useful positive controls in identifying additional $p70\beta^{S6k}$ substrates.

Kinase assays to measure the ability of the agent to modulate the kinase activity of a protein of the invention are widely available such as the assays disclosed by Mishima et al. (1996) J. Biochem. 19: 906-913) and Michnoff et al. (1986) J.

*Biol. Chem.* 261: 8320-8326. Alternative assay formats include actin-myosin motility assays such as those disclosed by Kohama et al. (1996) *TIPS* 17: 284-287 or Warrick et al. (1987) *Ann. Rev. Cell. Biol.* 3: 379421.

Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a non-random basis which takes into account the sequence of the target site and/or its conformation in connection with the agent's action. As described in the Examples, there are proposed binding sites for ATP/GTP and calmodulin as well as cAMP/cGMP kinase sites, TyrP sites and Ser/Thr kinase (catalytic) sites in the protein having SEQ ID No. 2. Agents can be rationally selected or rationally designed by utilizing the peptide sequences that make up these sites. For example, a rationally selected peptide agent can be a peptide whose amino acid sequence is identical to the ATP or calmodulin binding sites or domains.

The agents of the present invention can be, as examples, peptides, small molecules, vitamin derivatives, as well as carbohydrates. A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of proteins of the invention. Antibody agents are obtained by immunization of suitable mammalian subjects with peptides, containing as antigenic regions, those portions of the protein intended to be targeted by the antibodies.

J. Uses for Agents that Modulate at Least One Activity of the S6 Kinase Protein.

As provided in the Examples, the proteins and nucleic acids of the invention, such as the protein having the amino acid sequence of SEQ ID No. 2, are involved in ribosomal function. Agents that modulate or down-regulate the expression of the protein or agents such as agonists or antagonists of at least one activity of the protein may be used to modulate biological and pathologic processes associated with the protein's function and activity.

As used herein, a subject can be any mammal, so long as the mammal is in need of modulation of a pathological or biological process mediated by a protein of the invention. The term "mammal" is meant an individual belonging to the class Mammalia. The invention is particularly useful in the treatment of human subjects.

As used herein, a biological or pathological process mediated by a protein of the invention may include binding of substrates such as ATP, GTP or calmodulin or phosphorylation of a substrate, such as the S6 protein.

Pathological processes refer to a category of biological processes which produce a deleterious effect. For example, expression or up-regulation of expression of a protein of the invention may be associated with certain diseases. As used herein, an agent is said to modulate a pathological process when the agent reduces the degree or severity of the process. For instance, a disease may be prevented or disease progression modulated by the administration of agents which reduce or modulate in some way the expression or at least one activity of a protein of the invention.

The agents of the present invention can be provided alone, or in combination with other agents that modulate a particular pathological process. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents which modulate expression or at least one activity of a protein of the invention. While individual needs vary, determination of optimal ranges of effective amounts of each component is within the skill of the art. Typical dosages comprise about 0.1 to 100 µg/kg body weight. The preferred dosages comprise about 0.1 to 10 µg/kg body weight. The most preferred dosages comprise about 0.1 to 1 µg/kg body weight. In tissue culture, optimal dosage ranges for drugs such as wortmannin and rapamycin range from about 500 pM to about 1000 nM. Less optimum ranges include about 10 pM to about 10 mg.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice. The compounds of this invention can be utilized in vivo, ordinarily in mammals, such as humans, sheep, horses, cattle, pigs, dogs, cats, rats and mice, or in vitro.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Amino Acid Sequence of $p70\beta^{S6k}$ and Comparison With $p70\alpha^{S6k}$

Materials and Methods. Restriction enzymes and DNA modification enzymes were obtained from standard commercial sources and used according to manufacturer's recommendations. Oligonucleotides which were used for sequencing of $p70\beta^{S6k}$ and various PCR fragments were synthesized by Genosys or Japan Bioservice, Inc. The pcDNA1 and pcDNA3 mammalian expression vectors were from Invitrogen. The pGEX4T vector, glutathione-Sepharose-4B and HiTrapQ columns were purchased from Pharmacia cDNA of rat p70α-I was a gift from Dr. Joseph Avruch (Diabetes Unit, Massachusetts General Hospital). Rapamycin and PDGF BB were purchased from Calbiochem. Wortmannin was purchased from Sigma.

Cell cultures and Antibodies. A porcine aortic endothelial cell line (PAE-PDGF-R), stably expressing the human PDGF-β receptor, was maintained in HAM's F12 medium containing 10% fetal calf serum (FCS). CHO cells stably overexpressing human insulin receptors (CHO-IR cells) and HEK293 cells were maintained and cultured as described earlier (Hara et al., 1998 *J. Biol. Chem.* 273: 14484-14494) in HAM's F12 medium or Dulbecco's modified Eagles minimal essential medium (DMEM) supplemented with 10% FCS, respectively. Anti-FLAG monoclonal M2 antibody was purchased from Eastman Kodak Corp. Anti-phosphopeptide antibodies against proline-directed site Ser434 of p70α-I were purchased from New England Biolabs. Polyclonal antibodies raised against the C-terminal 104 amino acids fragment of $p70\alpha^{S6k}$ were from Dr. Joseph Avruch. A GST fusion protein containing amino acids 443-495 of $p70\beta^{S6k}$ (p70βC Ab) was used to raise polyclonal antibodies specific for $p70\beta^{S6k}$. Immunoreactive sera were affinity-purified on an Affigel matrix containing the GST/$p70\beta^{S6k}$-terminal fusion protein.

Fractionation of cell extracts. HEK293 cells were starved in DMEM medium for 16 h and then treated with 15% FCS for 10 min or 200 nM rapamycin for 30 min. After treatment, cells were lysed in ice-cold buffer A (20 mM Tris/HCl pH 7.5, 20 mM NaCl, 1 mM EDTA, 5 mM EGTA, 20 mM β-glycerophosphate, 1 MM-DTT, 1 mM PMSF, 2 mg/ml aprotinin, 10 mg/ml leupeptin) and the lysates centrifuged at 4° C. for 20 min at 10,000×g. Supernatants were filtered through a 0.45 μM filter and then loaded onto a HighTrapQ Sepharose column (1.0 ml column volume) equilibrated in Buffer A. The column was washed extensively in buffer A and build proteins eluted with a linear gradient of NaCl (20-500 mM). Aliquots of eluted proteins were subjected to SDS-PAGE and immunoblotted with anti-phosphopeptide antibodies directed against proline-directed site Ser434 of $p70\alpha^{S6k}$ or anti-peptide antibodies against the carboxyl terminal end of $p70\beta^{S6k}$.

Construction and screening of a HEK293 Uni-ZAP library and DNA sequencing analysis. Total RNA was isolated from HEK293 cells as described (Hara et al., 1998; Chomczynski et al., 1987 *Analytical Biochem.* 162: 156-159), and poly(A)+ mRNA was selected by using Dynabeads mRNA purification kit (Dynal). An oligo(dT)-primed library was constructed in UNI-ZAP XR vector from 5 mg of HEK293 mRNA, using the Uni-ZAP cDNA synthesis kit (Stratagene). Packaging into phages was carried out by using Gigapack III Gold Packaging extracts (Stratagene). The cDNA encoding full length $p70\beta^{S6k}$ kinase was isolated by screening 1×10$^6$ primary phages from HEK293 Uni-ZAP library with a $^{32}$P-labeled 0.65 Kb EcoRI/NotI fragment derived from the EST clone GenBank Accession No. AA410355 (Hillier et al., published on GenBank, 1997). Positive clones were confirmed, isolated in second-round screening and rescued as Bluescript plasmids by in vivo excision (Stratagene). PCR amplification and restriction mapping were used for primary characterization of isolated clones. Sequencing analysis of selected clones was performed on an Applied Biosystem 373A DNA automatic sequencer (PE Applied Biosystems).

Results. The $p70\alpha^{S6k}$ is activated by multiple phosphorylation within the pseudosubstrate and catalytic domains in response to extracellular stimuli, including serum, growth factors and hormones. Phosphospecific antibodies directed against phosphorylated sites of $p70\alpha^{S6k}$ have been recently developed: Phospho-$p70\alpha^{S6k}$ (Ser434) and Phospho-$p70\alpha^{S6k}$ (Thr444/Ser447). Both antibodies were shown to recognize specifically phosphorylated forms of $p70\alpha^{S6k}$, and this recognition was found to be sensitive to rapamycin. To compare the phosphorylation state and chromatographic behavior of $p70\alpha^{S6k}$ from cells stimulated with serum and treated with or without rapamycin, HEK293 cells were starved in DMEM medium for 16 h and then stimulated with 15% serum for 10 min prior treatment with or without 200 nM of rapamycin for 30 min. Cell extracts were fractionated using HighTrapQ Sepharose columns. Proteins were resolved on SDS-PAGE and immunoblotted with anti-phosphopeptide antibodies Ser434 and S444/T447 or antibodies specific for $p70\alpha^{S6k}$. In total lysates of serum stimulated HEK293 cells, this antibody recognizes specifically phosphorylated versions of $p70\alpha^{S6k}$ isoforms (p70 and p85). However, when cell lysates were fractionated and separated on SDS-PAGE, several additional bands appeared on the immunoblot together with the p70 and p85 isoforms of $p70\alpha^{S6k}$, including p190, p110, p90 and p60 (not shown). It is important to note that the recognition of these proteins by phosphospecific S434 antibodies was sensitive to rapamycin, indicating the specificity for the phosphorylated epitope. As expected, the anti-peptide antibodies specific for the $p70\alpha^{S6k}$ recognized 85-kDa and 70-kDa bands, which correspond to p70α-I and p70α-II, respectively. S434 is located in the autoinhibitory region of the $p70\alpha^{S6k}$, which is highly conserved among different species of $p70\alpha^{S6k}$, including *Drosophila* (Stewart et al., 1996 *Proc. Natl Acad. Sci. USA* 93: 10791-10796; Watson et al., 1996 *Proc. Natl Acad. Sci. USA* 93: 13694-13698). As phosphorylation of the S434 site is sensitive to rapamycin, it is possible to speculate that p190, p110, p90 and/or p60 may represent novel rapamycin-sensitive $p70\alpha^{S6k}$-related kinases.

Molecular cloning of novel $p70\alpha^{S6k}$. Peptide sequences which were used for raising anti-phosphopeptide antibodies S434 of p70α-I were taken to search the expressed sequence tag (EST) databases. This search generated hundreds of EST clones that showed high degree of homology to the query sequence. Extensive analysis of these clones allowed us to isolate several clones which were highly homologous to the 434 peptide, but did not match to cDNA clones from EMBL or Swissprot databases. Further characterization of these sequences indicated that two nearly identical clones (GenBank Accession Nos. AA284234 and AA410355) exhibited strong homology to the kinase extension domain of the protein kinase A (PKA) family of serine/threonine (S/T) kinases. Additionally, the homology in the kinase extension domain extended into the putative autoinhibitory domain, which is unique for the p70α$^{S6k}$, (less than 75% identity between p70α$^{S6k}$ and the unknown potential S6 kinase). However, the homology with p70α$^{S6k}$ dropped significantly downstream of the kinase extension and autoinhibitory domains, suggesting that these clones encoded a novel kinase of this family. Based on these data, we decided to further characterize these clones. Both EST clones were obtained from the UK HGMP Resource Center. Restriction mapping indicated that the GenBank Accession Nos. AA284234 and AA410355 clones contain short inserts of 0.6 kB and 0.65 kB respectively. Sequence analysis showed that these clones are identical to each other in an overlapping region and may encode a partial open reading frame (ORF), which shows very strong homology to the kinase extension and autoinhibitory domains of the p70α$^{S6k}$. These ESTs did not contain a full gene nor was there a protein coding sequence previously identified in these ESTs. Furthermore, four of the five proline-directed Ser/Thr phosphorylation sites located in an autoinhibitory pseudosubstrate domain of p70α$^{S6k}$ were conserved in the clones of p70β$^{S6k}$. Immediately after the autoinhibitory pseudo-substrate domain, the homology between p70α$^{S6k}$ and p70β$^{S6k}$ was very low (12% identity). Taking in account these findings, we proceeded to clone the full length cDNA clone encoding this potentially novel kinase.

Since several rapamycin-sensitive bands were found in the HEK293 cells with the use of anti-Ser434 phosphospecific antibodies, a library from this cell line was created. We screened 10$^6$ primary clones from the Uni-Zap/HEK293 library with a full length insert from EST clone AA410355 and isolated 12 positive clones. Sequence analysis of rescued plasmids allowed us to identify one clone, which contained an open reading frame of 495 amino acids (FIG. 2A). The C-terminus of this clone was found to be identical to the sequence of the EST clone AA410355, which was used for screening.

By analogy to p70α$^{S6k}$, the novel cDNA, encoding p70β$^{S6k}$, could potentially encode two isoforms as a result of alternative start codons. If this is the case, the shorter isoform may utilize an ATG codon which is 13 amino acids (aa) downstream of the first methionine and may encode a protein of 482 amino acids. Two potential isoforms were termed p70β-I (495 aa long) and p70β-II (482 aa long). The presence of additional 13 aa at the N-terminus of p70β-I isoform may determine its subcellular localization in the nucleus due to the presence of a putative nuclear localization sequence (RGRRARG, amino acid numbers 3-9 of SEQ ID No. 2). The overall structure of p70β$^{S6k}$ is similar to that of p70α$^{S6k}$. p70α$^{S6k}$ and p70β$^{S6k}$ share 70% identity and 85% similarity on protein level. The p70β$^{S6k}$ kinase consists of the amino-terminal non-catalytic region, a catalytic domain, a kinase extension and a carboxyl-terminal non-catalytic tail, whose amino acid identity corresponds to domains of p70α$^{S6k}$ is 40%, 83%, 80%, and 47%, respectively (FIG. 2B). The strong argument that this clone encodes a novel p70 S6 kinase is the presence of the autoinhibitory pseudosubstrate domain, which is not present in any other known kinases.

p70α$^{S6k}$ undergoes a multi-site phosphorylation in response to stimulation by insulin or mitogens. Such multiple phosphorylation sites are also well conserved in p70β$^{S6k}$ (FIG. 2B). It also contains 3 sets of phosphorylation sites, similar to p70α$^{S6k}$: (i) a set of Ser/Thr-Pro motifs clustered in an autoinhibitory pseudosubstrate domain (Ser423, Ser430, Ser436, Ser441 in p70p5 correspond to Ser 434, 441, and 447, Ser 452 in p70α$^{S6k}$; (ii) a second set includes Ser383 and Thr401 which is located in the kinase extension domain and corresponds to Ser394 and Thr412 in p70α$^{S6k}$; (iii) a third set consists of Thr251 which resides in the activation T-loop of kinase domain and corresponds to Thr252 in p70α$^{S6k}$. The greatest difference between the p70α$^{S6k}$ and the p70β$^{S6k}$ sequences are in the amino-terminal non-catalytic region (40% identity and 60% similarity) and the carboxyl-terminal non-catalytic tail (47% identity and 66% similarity). p70β$^{S6k}$ also contains proline-rich sequences at the C-terminus, that may mediate the interaction with SH3-domain-containing molecules.

Example 2

Tissue Specific Expression of p70β$^{S6k}$

Materials and Methods. Northern blot analysis was performed using commercial nylon membranes pre-bound with 2 μg of gel-separated poly(A)+ RNA samples obtained from various human tissues or tumor cell lines from Clontech. The following probes were used for the detection of p70α$^{S6k}$ and p70β$^{S6k}$ messages: (i) a 476-base pair (bp) HindIII fragment spanning 56 bp of 3' end coding region and 420 bp of 3' non-coding region of the human p70α$^{S6k}$ (EST clone, AA425599), (ii) a 650-bp fragment spanning 518 bp upstream of the stop codon and about 130 bp of non-coding region of the human p70β$^{S6k}$ (EST clone, AA410355). Human β-actin cDNA probe was used as a negative control (Clontech). These probes were labeled by Multiprime DNA labeling system (Amersham) and separated from unincorporated [γ$^{32}$P]dCTP by Nuctrap push columns (Stratagene). Northern blots were pre-hybridized with ExpressHyb solution and hybridized with labeled probes according to manufacturer's recommendations. After extensive washing with 2×SSC, 0.05% sodium dodecyl sulfate (SDS) at room temperature, and twice with 0.1×SSC, 0.1% SDS at 50° C., the localization of bound probes on membranes was identified by autoradiography or with the use of the PhosphoImager.

Figure 3A:
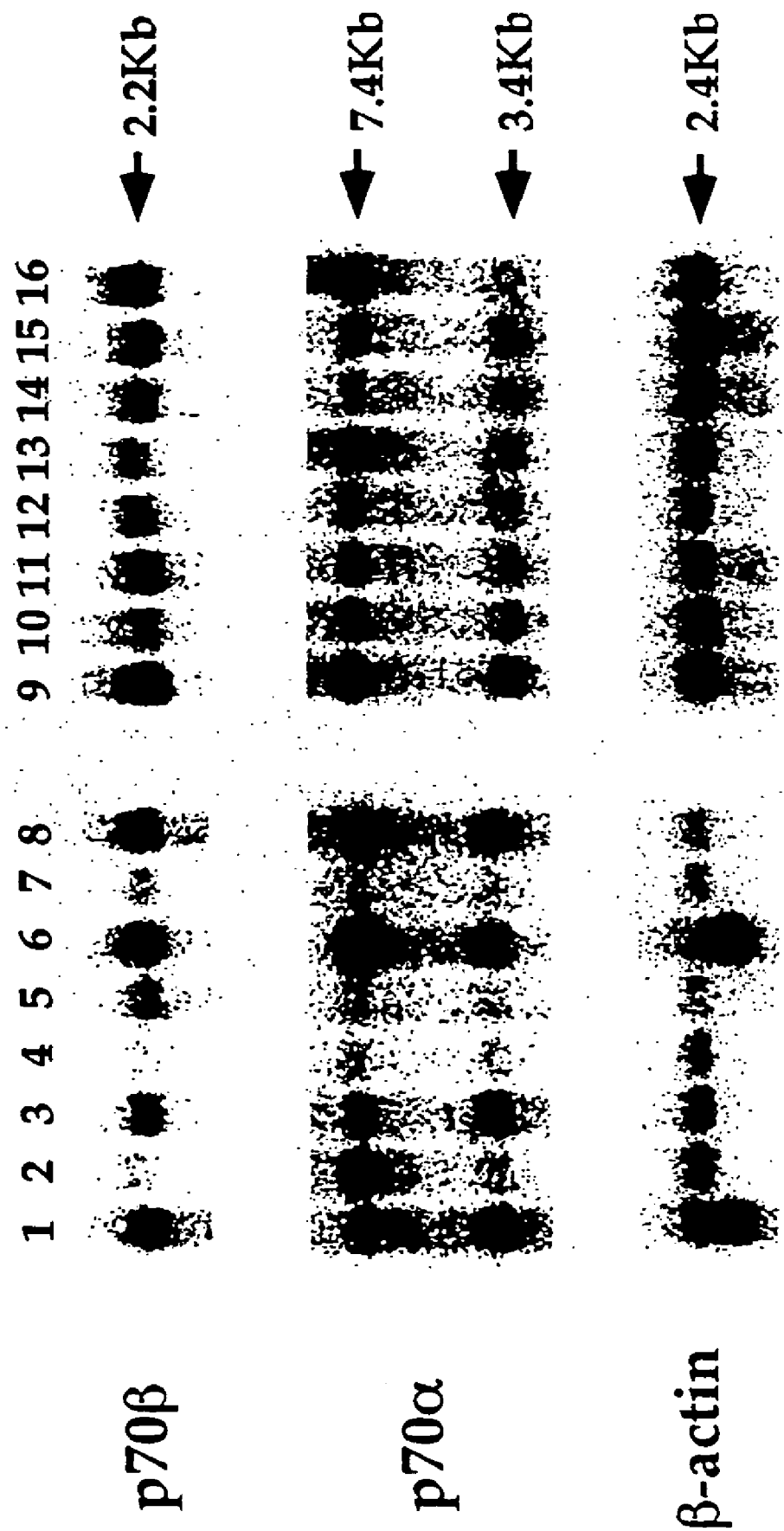
FIG. 3A-3B. Tissue Specific Expression of p70β$^{S6k}$. Northern blot analysis of poly(A)+ RNA from human tissues (FIG. 3A) and tumor cell lines (FIG. 3B).

Results. In order to compare expression patterns of p70α$^{S6k}$ and p70β$^{S6k}$ in human tissues and cell lines, 3' prime coding and non-coding regions, which exhibit low level of homology between both the α and β S6 kinases, were used as probes. Northern blot analysis using poly(A)+ RNA isolated from human tissues revealed a single 2.2 kb transcript for p70β$^{S6k}$, while p70α$^{S6k}$ probe specifically hybridized to 3.4 kb and 7.4 kb transcripts (FIG. 3A). The expression pattern of p70α$^{S6k}$ and p70β$^{S6k}$ transcripts is remarkably similar, showing ubiquitous expression in all tissues. Highest expression levels were found in spleen, skeletal muscle and peripheral blood leukocytes, whereas brain, lung and kidney showed the lowest expression of transcripts for both S6 kinases. The only significant difference on the level of mRNA expression between p70α$^{S6k}$ and p70β$^{S6k}$ was found in liver. The expression of p70β$^{S6k}$ mRNA in liver is 2-3 times higher than that of p70α$^{S6k}$. Liver possesses a high concentration of p70α$^{S6k}$ and was originally used by several groups to purify p70α$^{S6k}$ for biochemical studies and protein sequencing analysis (Banerjee et al., 1990 *Proc. Natl Acad. Sci. USA* 87: 8550-8554; Kozma et al., 1990 *Proc. Natl. Acad. Sci. USA* 87: 7365-7369).

Figure 3B:
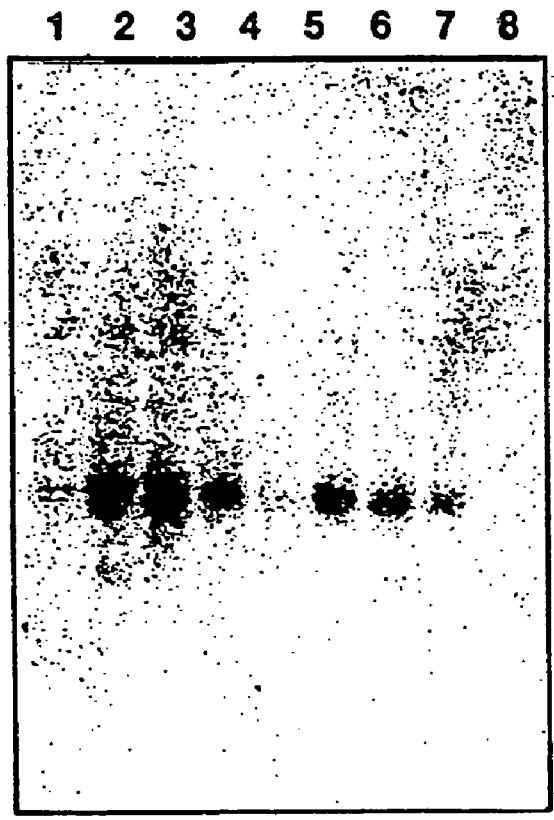

We also analyzed the expression of p70β$^{S6k}$ mRNA in tumor cell lines using the same probe as for the analysis of tissue distribution. A single transcript of the same size as in human tissues, 2.2 kb, was found to be highly expressed in HeLa and K562 cells, but was barely detectable in HL-60, MOLT-4 and melanoma G361 cell lines (FIG. 3B).

Example 3

Phosphorylation of the Ribosomal Protein S6 and its C-Terminal Synthetic Peptide by p70α$^{S6k}$ and p70β$^{S6k}$ Materials and Methods. Expression of GST/p70β$^{S6k}$ fusion protein in bacteria. A PCR-based strategy was used to make a bacterial expression plasmid for GST/p70β$^{S6k}$ fusion protein. A cDNA fragment encoding 443-495 amino acids of p70β$^{S6k}$ was amplified by PCR and cloned into the pGEX4T expression vector (Pharmacia). This construct was transformed into *E. coli* XL1-Blue competent cells (Stratagene) and the expression of the GST/p70β$^{S6k}$ fusion protein was induced by isopropyl β-D-thiogalactopyranoside (IPTG). The GST/p70β$^{S6k}$ fusion protein was purified by using glutathione-Sepharose-4B beads according to manufacturer's recommendation (Pharmacia). After SDS-PAGE analysis, affinity purified fusion proteins were dialyzed against 20 mM (Tris pH 7.4), 150 mM NaCl, 50% Glycerol and stored at −20° C. This preparation of the GST/p70β$^{S6k}$ C-terminal fragment was used for the production of polyclonal antibodies specific for p70β$^{S6k}$.

Construction of mammalian expression plasmids. The full length coding sequence, corresponding to the p70β-I (1495 amino acids) was amplified by PCR using human cDNA clone N53 isolated from HEK293 library as a template and a panel of specific oligonucleotides. Amplified constructs were digested with appropriate enzymes, gel purified and cloned into the pcDNA1 vector in-frame with N-terminal FLAG epitope.

Amino-terminal EE-tagged p70α-II and p70α-II constructs were created by a PCR-based cloning strategy. This was achieved by using specific oligonucleotides containing BE-tag sequence and appropriate restriction sites. The cDNA encoding full length human p70β$^{S6k}$ (clone 53) and rat p70α$^{S6k}$ were used as templates. The resulting PCR fragments were digested with restriction enzymes, gel purified and cloned into the pcDNA3 expression vector. The construction of the pMT2 FLAG p70α-I was described previously (Hara et al., 1998). All constructs generated by a PCR-based approach were verified by sequencing. A Qiagen plasmid Midi kit was used to purify plasmid DNAs for transient transfections. The introduction of the FLAG-tag and the EE-tag sequences at the N-terminus of p70α$^{S6k}$ and p70β$^{S6k}$ allows the study of recombinant proteins via the use of specific antibodies.

Results. To test if the isolated p70β$^{S6k}$ cDNA would encode a functional kinase capable of phosphorylating ribosomal protein S6, a cDNA fragment encoding a short version of p70β$^{S6k}$ (p70β-II) was subcloned into mammalian expression vector in frame with EE-tag or Flag-tag epitopes. These constructs were transfected into HEK293 cells using lipofectAMINE under conditions recommended by the manufacturer. The expression of recombinant p70β$^{S6k}$ was analyzed by immunoprecipatation or western blotting with EE-tag or Flag-tag antibodies. Both constructs express the protein of approximately 60 kDa The expression level of p70β$^{S6k}$ was comparable to that of p70α-I and p70α-II isoforms, when expressed in HEK293 cells.

Anti-p70β$^{S6k}$ polyclonal antibodies were generated using synthetic peptides corresponding to the carboxy terminal 15 amino acids of p70β$^{S6k}$. These peptides were coupled to KLH and then injected into rabbits using standard procedures. Immune sera was purified using Affigel beads containing covalently cross-linked carboxy terminal peptide.

Figure 4B:
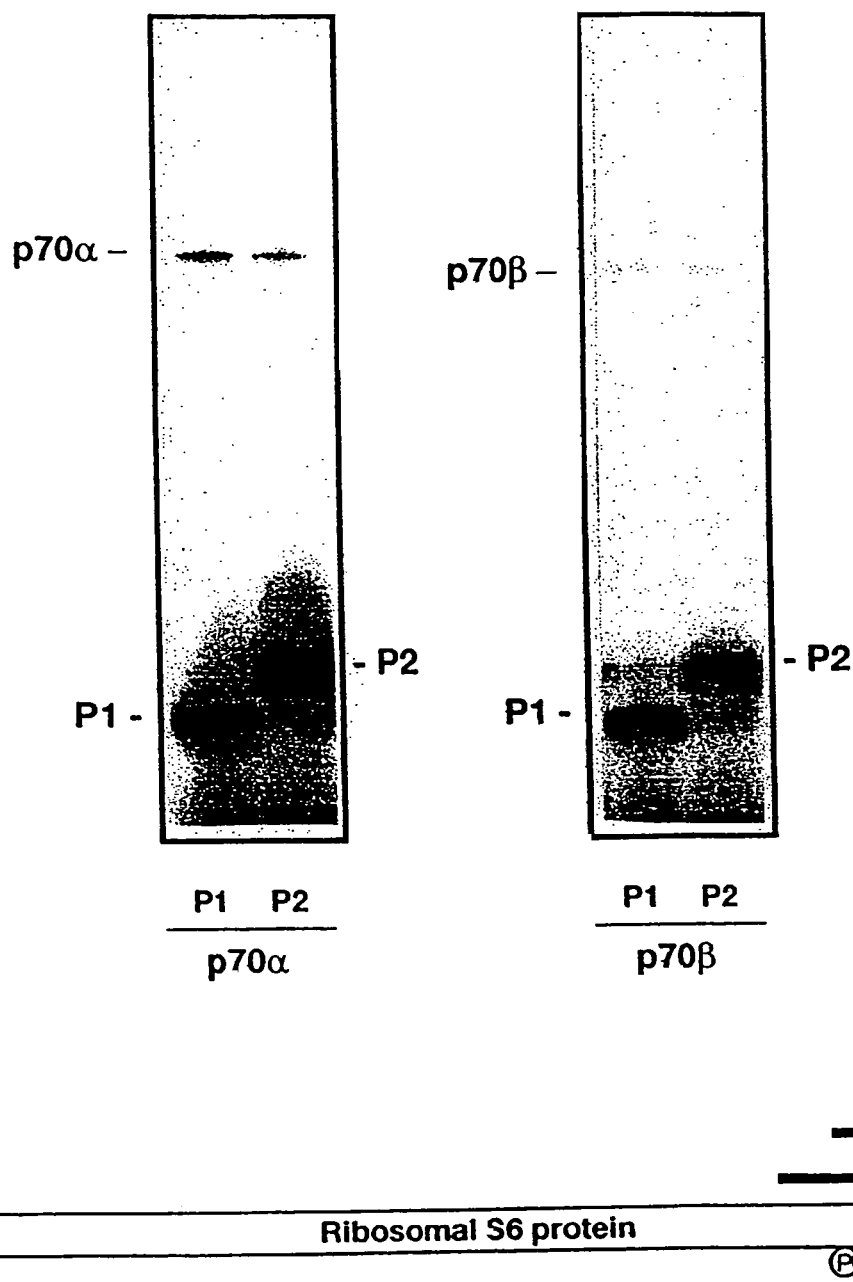

To determine whether the putative p70β$^{S6k}$ was indeed a novel ribosomal protein S6 kinase, the recombinant p70β$^{S6k}$ was expressed in HEK293 cells, immunoprecipitated with anti-EE-tag antibodies and an in vitro kinase reaction performed in the presence of purified 40S ribosomal subunit. As shown in FIG. 4A, p70β$^{S6k}$ (p70β-II isoform) phosphorylates the S6 protein in vitro nearly as efficiently as p70α$^{S6k}$. We also tested the ability of p70β$^{S6k}$ (p70β-II isoform) to phosphorylate a synthetic peptide representing C-terminus of S6 protein, which contains all sites known to be phosphorylated by p70α$^{S6k}$. FIG. 4B demonstrates that p70β$^{S6k}$ (p70β-II isoform) also phosphorylates this peptide but with slightly lower efficiency than observed with p70α$^{S6k}$. Therefore, p70β$^{S6k}$ (p70β-II isoform) may not phosphorylate the same sites of the ribosomal protein S6 as does p70α$^{S6k}$.

The intrinsic activity of the p70β$^{S6k}$ is significantly lower than p70α$^{S6k}$. The absence of one phosphorylation site in the autoinhibitory domain of p70β$^{S6k}$ may be responsible for this decrease in intrinsic activity.

Example 4

Stimulation of p70β$^{S6k}$ Activity by Insulin, Serum and TPA

Materials and Methods. HEK293 cells or CHO-IR cells were transfected with plasmids containing p70α$^{S6k}$ and p70β$^{S6k}$ sequences using lipofectAMINE under conditions recommended by the manufacturer (Gibco-BRL). Two days later, transfected cells were frozen in liquid nitrogen and stored until lysis. After cell extraction, the lysates were subjected to immunoprecipitation and/or immunoblot analysis. If cells were to be stimulated, they were starved in medium without FCS for 16 h and then stimulated with 10$^{-7}$ M insulin for 10 min, 15% FCS for 10 min, 500 nM TPA for 30 min or vehicle alone. PAE-PDGF-R cells were transfected with appropriate plasmids using lipofect under conditions recommended by the manufacturer. After 24 h transfected cells were serum-starved for 16 h and stimulated with 20 ng/ml PDGF BB (Calbiochem) for 20 min. Control cells were treated with the vehicle under the same conditions.

Figure 5A:
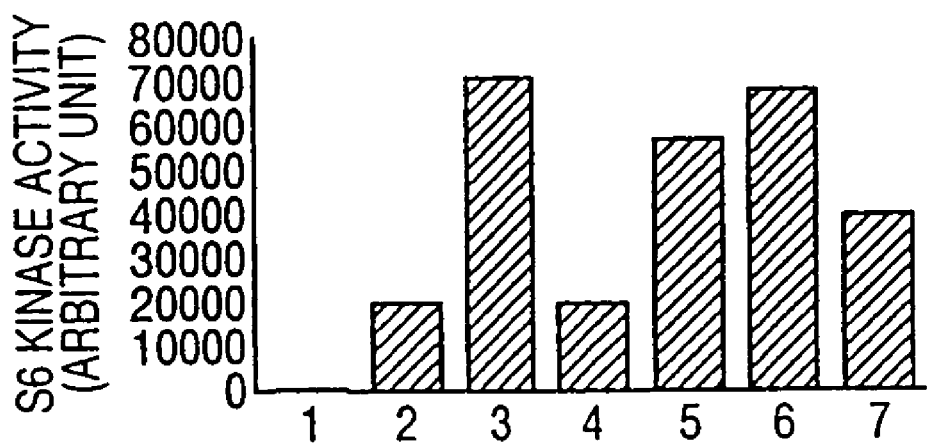

Results. The effect of various extracellular stimuli on the p70β$^{S6k}$ activity was studied in different cell lines, transiently transfected with Flag-tagged or EE-tagged versions of p70β$^{S6k}$. The activation of p70β$^{S6k}$ (p70β-II isoform) by insulin was analyzed in CHO-IR cells, which stably over expresses the insulin receptor. As shown in FIG. 5A, treatment of CHO-IR cells with insulin induces p70β$^{S6k}$ (p70β-isoform) activity towards ribosomal S6 protein by 2.8 fold. In the same cell line and under the same conditions, the activity of p70α$^{S6k}$ was activated 3.5 fold with insulin treatment (FIG. 5A). Almost equal amounts of p70α$^{S6k}$ and p70β$^{S6k}$ (p70-II isoform) were expressed in cells and used in an in vitro kinase assay after immunoprecipitation. In addition, both serum and TPA also stimulated p70β$^{S6k}$ (p70β-II isoform) phosphorylation of the ribosomal protein S6 (FIG. 5A).

Using PAE-PDGF-R cells, the activation of the p70α$^{S6k}$ and p70β$^{S6k}$ (p70β-II isoform) by PDGF was examined. This cell line stably over expresses the PDGF receptor, and the activation of p70α$^{S6k}$ in response to PDGF was shown to be very efficient (FIG. 5B). We found that PDGF stimulation of these cells leads to a rapid activation of recombinant p70β$^{S6k}$ (p70β-II isoform).

These data indicate that p70β$^{S6k}$ is activated by a number of extracellular stimuli in a very similar way as p70α$^{S6k}$. However, activation in the PAE-PDGF-R cells was 30 fold for p70β$^{S6k}$ and only 3.4 fold for p70α$^{S6k}$.

Example 5

Effects of Rapamycin and Wortmannin on p70β$^{S6k}$ and p70α$^{S6k}$

Materials and Methods. Treatment of transfected cells with rapamycin or wortmannin was performed as follows: 48 h after transfection, the cells were treated with various concentrations of rapamycin or wortmannin for 30 min.

Figure 6B:
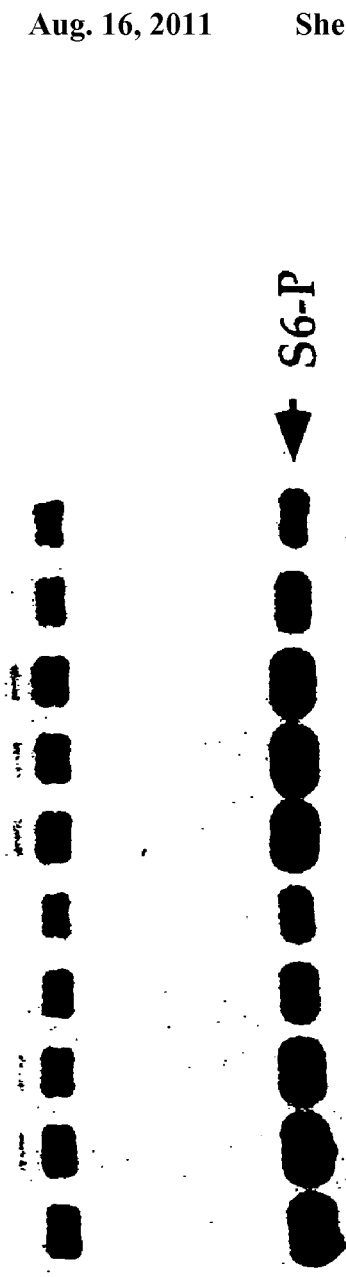

Results. These data in Examples 4 and 5 indicate that p70β$^{S6k}$ is activated by a number of extracellular stimuli in a similar fashion to p70α$^{S6k}$. The two fungal inhibitors, wortmannin and rapamycin, specifically inhibit activation of p70α$^{S6k}$ via PI3-kinase- and mTOR-dependent pathways respectively. Thus, the effects of both inhibitors on p70β$^{S6k}$ activity were examined. After p70α-I and p70β-II were transiently expressed in HEK293 cells, cells were maintained in DMEM containing 10% FCS and then treated with various concentrations of rapamycin or wortmnannin. We found that the activity of p70α$^{S6k}$ and p70β$^{S6k}$ were inhibited by rapamycin and wortmannin in a dose dependent manner (FIGS. 6A and B, upper panel). However, it appears that p70β$^{S6k}$ is less sensitive to rapamycin and wortmannin, when compared with p70α$^{S6k}$. This difference is more obvious at lower concentration of inhibitors. In the presence of 20 nM rapamycin the inhibition of the p70α$^{S6k}$ is 92%, while only 46% for p70β$^{S6k}$. Addition of 100 nM of wortmannin inhibits 86% of p70α$^{S6k}$ activity and 62% of p70β$^{S6k}$ activity. The inhibition of p70β$^{S6k}$ by rapamycin and wortmannin is lower than that observed for p70α$^{S6k}$ indicating different mechanisms of regulation exist for p70β$^{S6k}$.

Example 6

Interaction of the p70β$^{S6k}$ With Different GST/SH3 Fusion Proteins

Materials and Methods. The EE-tag/p70β$^{S6k}$ was transiently over expressed in HEK293 cells as described above. Transfected cells were lysed in buffer A (50 mM-Tris/HCl pH=8.0, 1% NP-40, 120 mM NaCl, 20 mM NaF, 1 mM EDTA, 6 mM EGTA, 20 mM sodium β-glycerophosphate, 1 mM DTT, 1 mM PMSF, 10 µg/ml leupeptin, 10 µg/ml pepstatin and 2 µg/ml aprotinin) two days after transfection. After centrifugation at 12,000 rpm for 20 min, the supernatants were incubated for 2 hrs with Protein A beads pre-coupled with anti-EE antibodies. Beads were washed with lysis buffer before different GST/SH3 fusion proteins (1.5 mg each) were added to separate immunoprecipitation reactions. Two hours later, beads were washed extensively in lysis buffer, bound proteins separated on the SDS-PAGE and transferred to the PVDF membrane. Specific interaction of the GST/SH3 domains with pre-bound EE-tag/p70β$^{S6k}$ was assessed by immunoblotting with the anti-GST antibodies.

Figure 7:
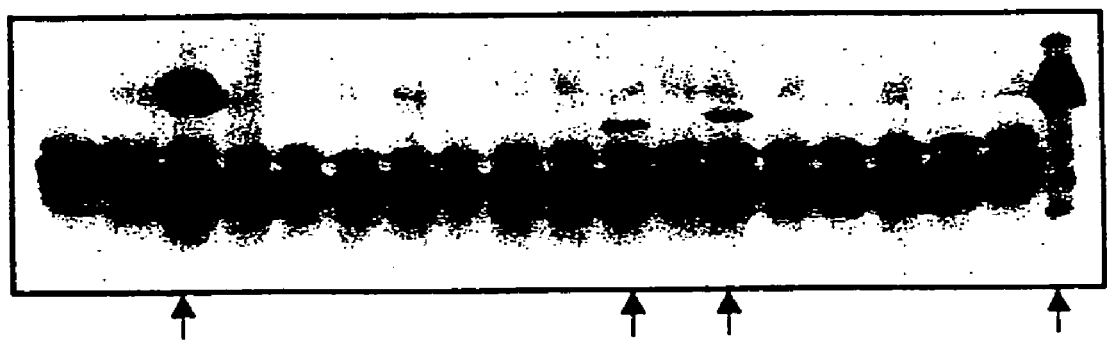
FIG. 7. Interaction of the p70β$^{S6k}$ with different GST/SH3 fusion proteins. HEK293 cells were transiently transfected with EE-tag/p70β$^{S6k}$. Two days later, cells were lysed and the lysates were immunoprecipitated with anti-EE antibodies. GST/SH3 fusion proteins (1.5 μg each) were incubated with anti-EE tag immunoprecipitates. Specific interaction with p70β$^{S6k}$ was measured by anti-GST immunoblotting. SH3 domains from different signaling and cytoskeletal proteins were expressed in bacteria as GST fusion proteins and purified nearly to homogeneity using glutathione-Sepharose beads. The GST/SH3 fusion proteins used are: GST (lane 1), p80α subunit of the PI3-kinase (lane 2), GAP (lane 3), PLCγ (lane 4), spectrin (lane 5), crk (lane 6), n-grb2 (lane 7), c-grb2 (lane 8), grb2 full (lane 9), csk (lane 10), fgr (lane 11), fyn (lane 12), src (lane 13), ruk a (lane 14), ruk b (lane 15), ruk c (lane 16), p15 (lane 17), profilin (lane 18) and GST/GAP control (lane 19). "I" indicates instances of binding between p70β$^{S6k}$ and a SH3 containing fusion protein.

Results. The C-terminus of the p70β$^{S6k}$ contains proline-rich sequences which are not present in p70α$^{S6k}$. Src-homology region 3 domains (SH3 domain) are present in many signaling and cytoskeletal molecules and interact specifically with proline-rich sequences which form left-handed helixes. Sequence analysis of the proline-rich region in p70β$^{S6k}$ indicates the presence of several putative SH3 domain binding motifs. Therefore, the ability of p70β$^{S6k}$ (p70β-II isoform) to interact with a panel of SH3 domains was examined. In this experiment, the EE-tag/p70β$^{S6k}$ was transiently over expressed in HEK293 cells and immunoprecipitated with anti-EE antibodies coupled to Protein G Sepharose. The resulting immunoprecipitates were incubated with different GST/SH3 domain fusion proteins. After extensive washing, specific interaction between p70β$^{S6k}$ and SH3 domains was analyzed by SDS-PAGE and immunoblotting with anti-GST antibodies. As shown in FIG. 7, several SH3 domains, including those of GAP, Src, Fgr exhibited specific interaction towards p70β$^{S6k}$.

Example 7

Immunoprecipitation and Western Blot Analysis of Transiently Expressed p70β-I and p70β-II Materials and Methods. Anti-p70β$^{S6k}$ polyclonal antibodies were generated using a synthetic peptide corresponding to the C-terminal tail of p70β$^{S6k}$. The peptide was coupled to KLH, and rabbits were immunized using standard procedures. Immune sera harvested obtained from the immunized rabbits was purified using affinity chromatography on Affigel beads containing covalently cross-linked C-terminal peptides of p70β$^{S6k}$.

Figure 8:
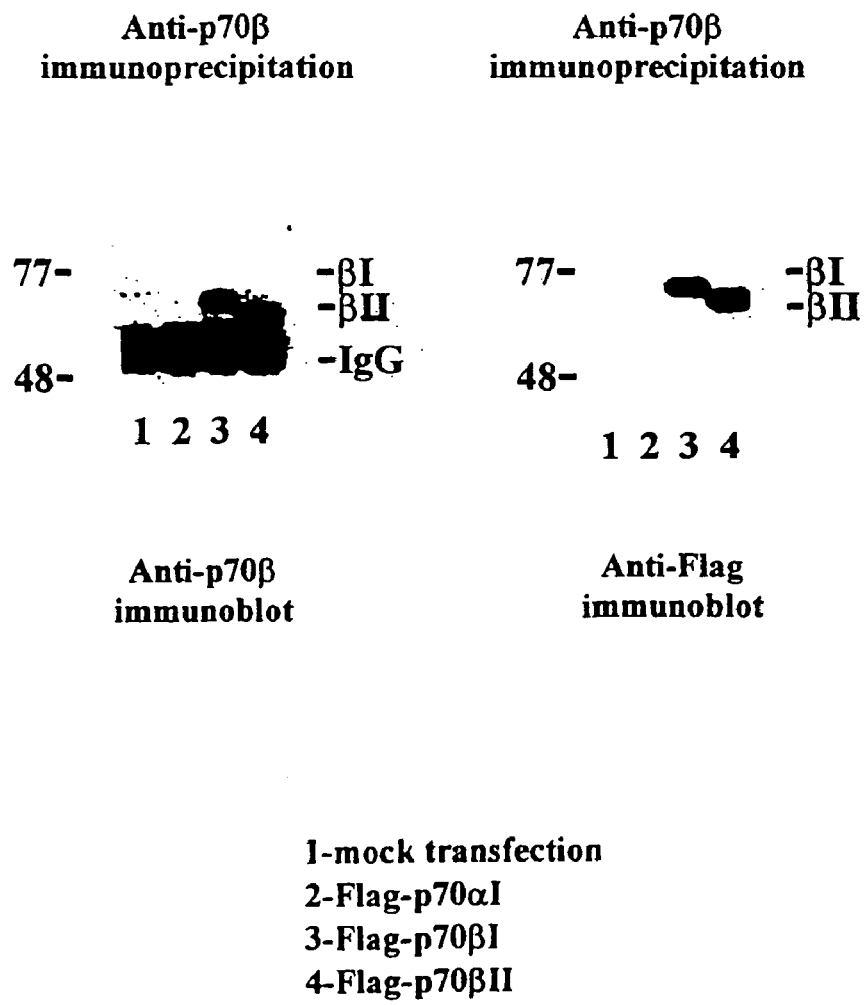
FIG. 8. Immunoprecipitation and Western blot analysis of the p70β-I and p70β-II isoforms transiently over expressed in HEK293 cells with anti-p70β$^{S6k}$ antibodies. The lanes are the same for each panel: mock transfected (lane 1), Flag-p70α-I transfected (lane 2), Flag-p70β-I transfected (lane 3), and Flag-p70β-II transfected (lane 4).

HEK293 cells were transfected with pcDNA1 along, pcDNA1/Flag-p70α-I, pcDNA1/Flag-p70β-I, or pcDNA1/Flag-p70β-II. Two days after transfection with one of these plasmids, cell lysates were prepared. Proteins were immunoprecipitated using the p70β$^{S6k}$ C-terminal affinity purified polyclonal antibodies or anti-Flag monoclonal antibodies. Immunoprecipitates were resolved on SDS PAGE and proteins transferred to PVDF membranes. The PVDF membranes were immunoblotted using anti-Flag monoclonal antibodies or p70β$^{S6k}$ C-terminal antibodies as indicated in FIG. 8.

Results. The expression of both p70β$^{S6k}$ isoforms was analyzed in HEK293 cells using anti-p70β$^{S6k}$ C-terminus specific polyclonal antibodies. Both p70β$^{S6k}$ isoforms were found to be specifically immunoprecipitated with anti-p70β$^{S6k}$ antibodies, but not p70α-I, as confirmed by anti-Flag and anti-p70β$^{S6k}$ immunoblotting. It was found that the p70β-I isoform which encodes a 495 amino acid protein, is translated into a protein which migrates in a SDS-PAGE gel at approximately 70 kD. The p70β-II isoform, which is a truncated form of p70β-I lacking 13 amino acids at the amino terminus of p70β-II, migrates in a SDS-PAGE gel at approximately 60 kD.

Example 8

Generation of Activated Variants of p70β$^{S6k}$ (T401D) and p70α$^{S6k}$ (T412D)

Materials and Method. Activated variants of p70β$^{S6k}$ and p70α$^{S6k}$ were made by site-directed mutagenesis. Oligonucleotide primers, specific to the site to be mutated and complimentary to opposite strands of p70β$^{S6k}$ and p70α$^{S6k}$ sequences were generated as recommended by manufacturer (Stratagene). Site directed mutagenesis was carried out using pcDNA3/Glu-tag-p70β$^{S6k}$ and pcDNA3/Glu-tag-p70α$^{S6k}$ expression vector/plasmids as templates, according to the recommended protocol (Stratagene). All mutations were verified by DNA sequencing. Expression of mutated forms of both kinases was analyzed by immunobloting with anti-Glu-tag antibodies. The activity of normal and mutated forms of both kinases was measured by in vitro S6 kinase assay. 40S ribosomal subunit was used as a substrate in this reaction.

Figure 9:
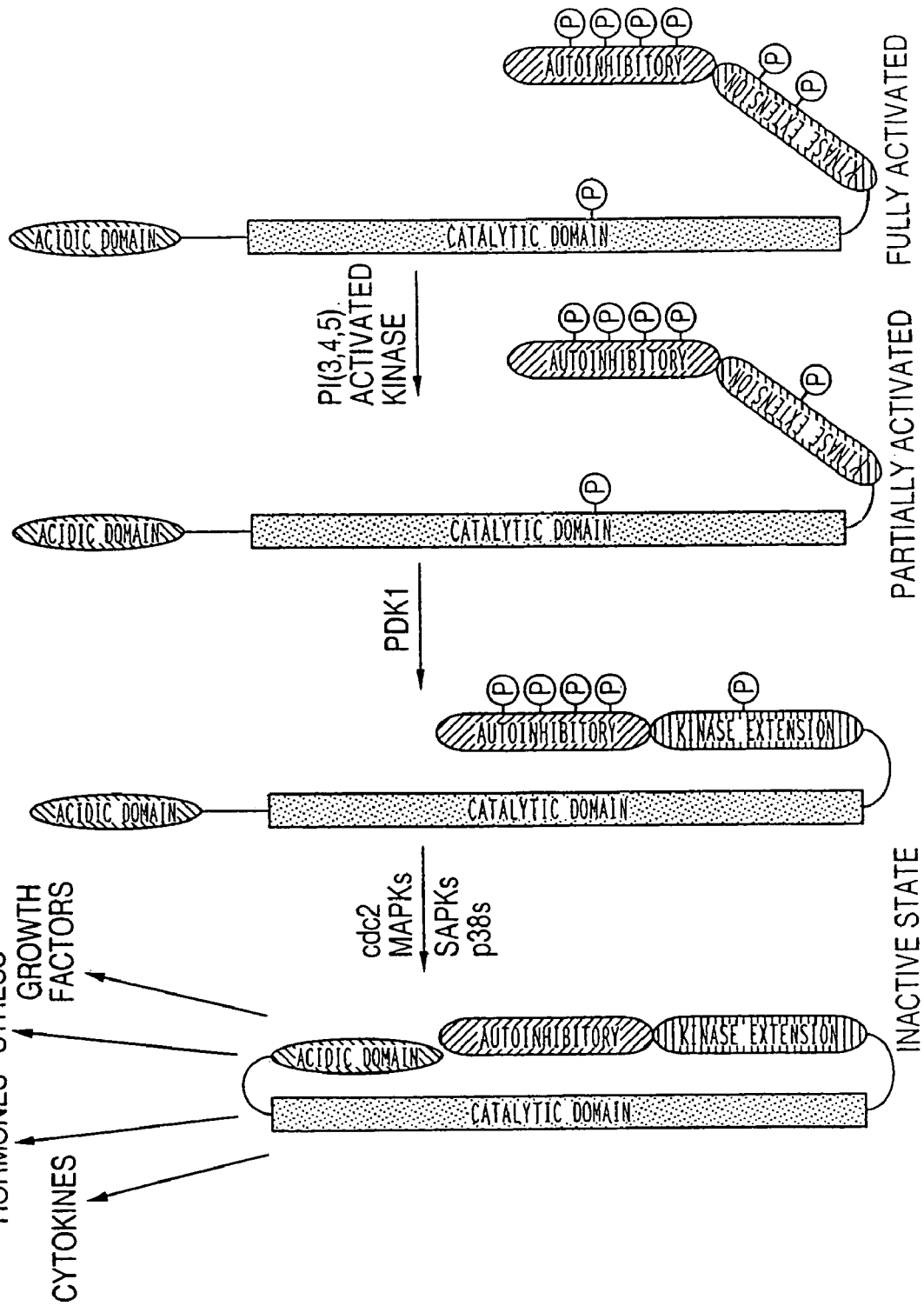
FIG. 9. A model for the activation of p70$^{S6}$ Kinase. Schematic presentation of the p70α$^{S6k}$ structure, protein-protein interactions, activation levels and phosphorylation state.

Results. Studies on p70α$^{S6k}$ demonstrate that this kinase is activated by multiple phosphorylations in response to growth factors or hormones (FIG. 9). A number of kinases that can phosphorylate p70α$^{S6k}$ in vitro and in vivo have been identified, including cdc2, MAPK, SAPK, p38, TOR and PDK1. However, very little is known about the process of dephosphorylation, which is essential for the inactivation of the kinase.

Figure 10:
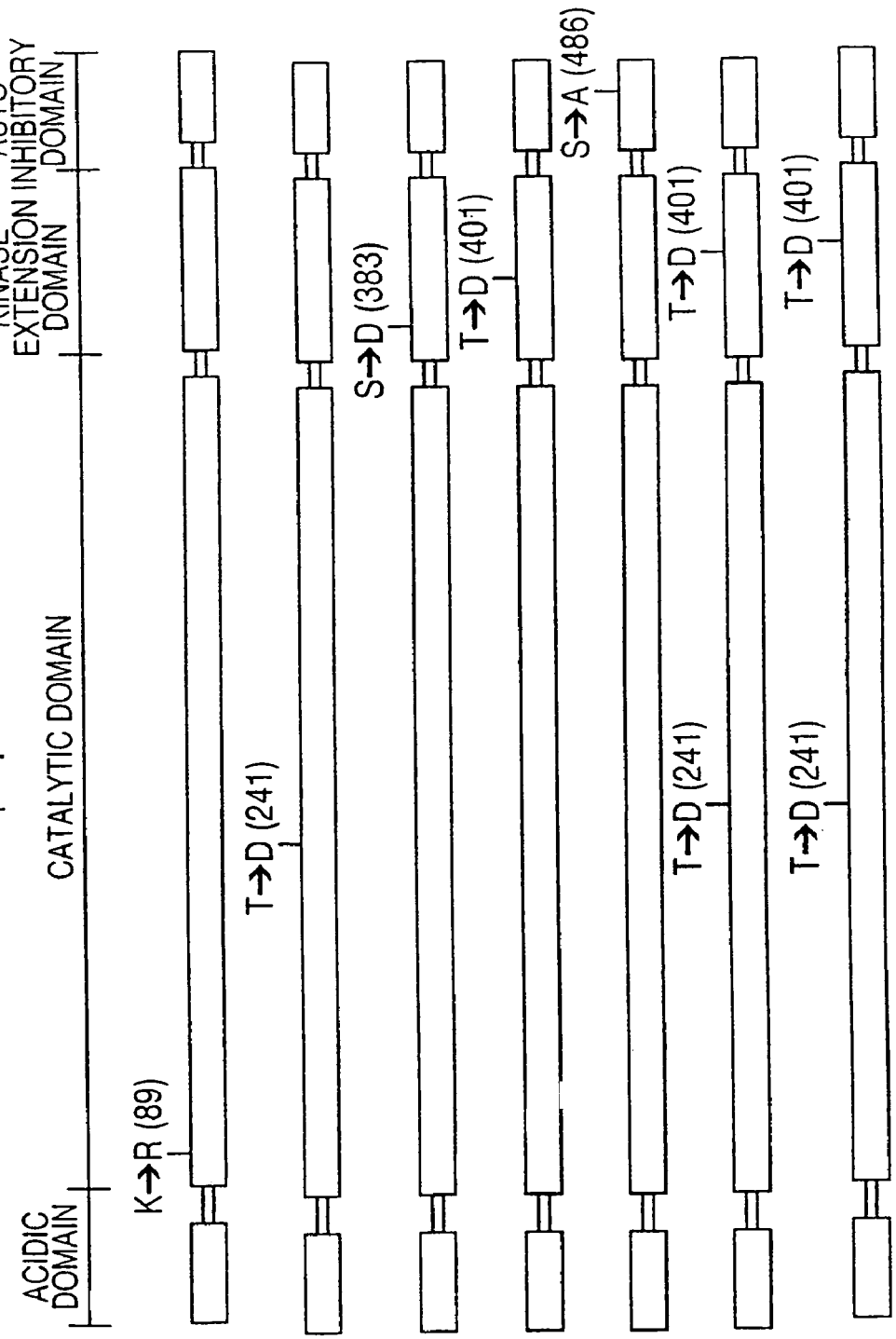
FIG. 10. p70β$^{S6k}$ mutations. Schematic presentation of substitution mutations engineered into p70β$^{S6k}$, including a change of Threonine at amino acid 401 to Aspartic acid (T401D).
Figure 11:
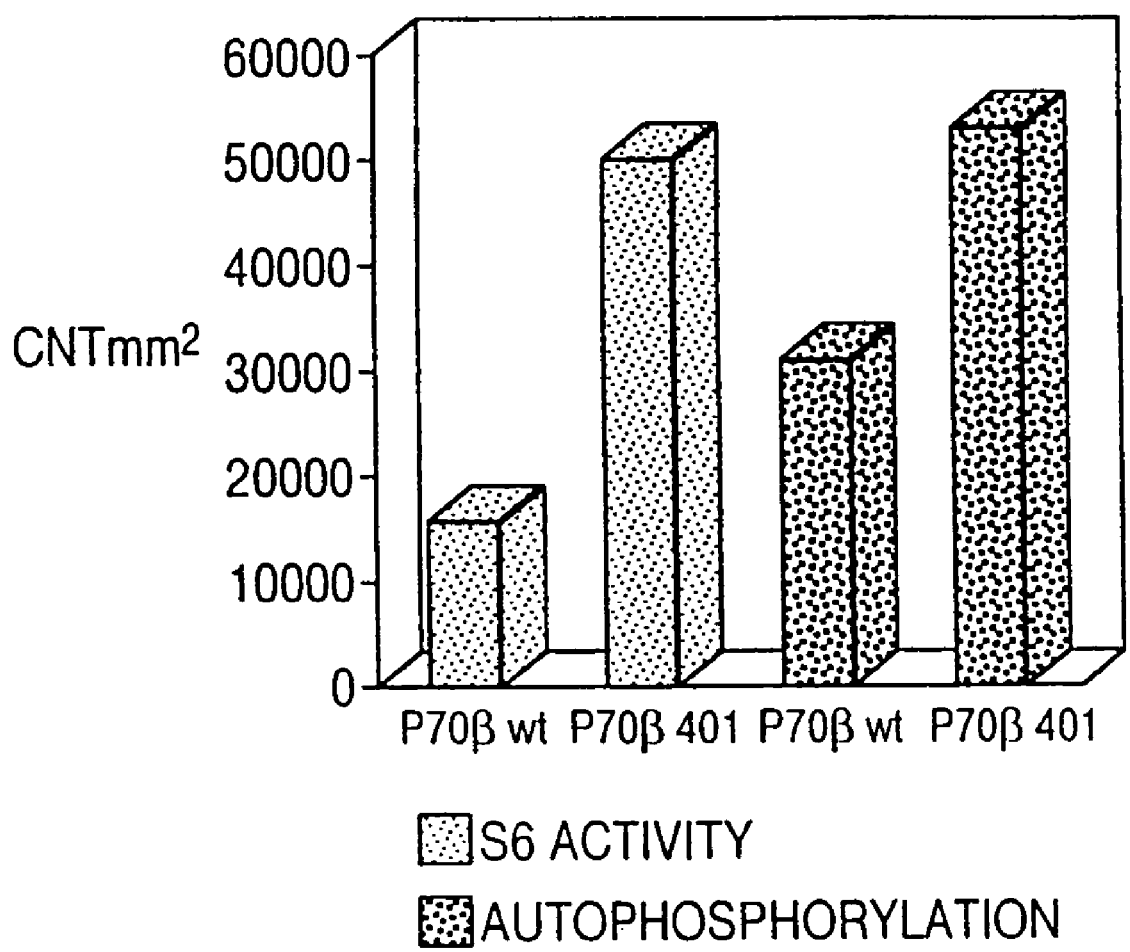
FIG. 11. p70β$^{S6k}$ (T401D) activity. Activity of p70β$^{S6k}$ (T401D) variant as compared to wt p70β$^{S6k}$ under S6 Kinase and autophosphorylation assays.

We have generated an activated form of p70β$^{S6k}$ by substituting putative phosphorylation site Thr 401 with Aspartic acid (Asp) ("p70β$^{S6k}$ (T401D)") as shown in FIG. 10. Transfection studies in HEK293 cells and S6 kinase assays indicated that p70β$^{S6k}$ (T401D) mutant is in an activated state in unstimulated cells, when compared with wild type kinase (3 times higher activity, as shown in FIG. 11). We have also created an activated version of p70α$^{S6k}$ (T412D), which showed a greater state of activation (18 fold activation, FIG. 12).

It will be apparent to the skilled artisan that activated variants of both kinases such as disclosed above can be used in the search for binding partners. Binding partners or molecules, such as phosphatases, are considered to form tighter and more stable complexes with such irreversibly activated kinases.

Example 9

Identification of p70β$^{S6k}$-Binding Partners

Materials and Methods. HEK293 cells are transfected using lipofectAMINE (as recommended by manufacturer, Gibco-BRL) with pcDNA3 expression vectors encoding activated variants of p70β$^{S6k}$ (T401D) and p70α$^{S6k}$ (T412D). Binding partners that preferentially associate with p70β$^{S6k}$ may be identified by comparing the profile of proteins precipitated from activated p70β$^{S6k}$ expressing cells to the profile of activated p70α$^{S6k}$ expressing cells and/or negative control cells. Cells transfected with the pcDNA3 plasmid alone, may be used as a negative control in this experiment. Two days after transfection, cells are lysed in extraction buffer: 50 mM Tris/HCl (pH8.0); 120 mM NaCl; 20 mM NaF; 20 mM b-glycerophosphate; 1 mM EDTA, (pH 8.0); 6 mM EGTA; 1% NP-40; 1 mM DTT. The following protease and phosphatase inhibitors are added to the extraction buffer just before cell lysis: 5 mM Benzamidine; 1 mM PMSF; 1 mg/ml of aprotinin; 0.125 mM NaVO4; Pepstatin; and Leupeptin.

The resulting cell lysate is centrifuged at 14,000 rpm for 20 min at 4° C. to remove the insoluble fraction. If the lysate is not used immediately it is stored at −80° C. until needed. The protein concentration of the samples is measured using a Coomassie Protein Assay reagent (Pierce) at 595 nm. An equal amount of supernatant from each sample is added to fresh 1.5 ml tubes and the volumes is equalized using lysis buffer. Affinity purified anti-Glu antibody is added to the supernatant and incubated on the wheel for 1 hr at 4° C. Protein-G sepharose beads, pre-washed in lysis buffer, are used to bring down immune complexes.

After extensive washing in lysis buffer (4×), 2× sample buffer is added to the beads. Bound proteins are eluted from the beads by boiling and separated by SDS-PAGE electrophoresis. Separated proteins are silver stained and the pattern of associated proteins is analyzed.

Results. The pattern of associated proteins are compared between activated variants of p70β$^{S6k}$ and p70α$^{S6k}$ kinases. Mutated variants of both kinases are transiently expressed in HEK293 cells as Glu-tag fusion proteins. The presence of a Glu-tag epitope at the N-terminus of p70β$^{S6k}$ and p70α$^{S6k}$ allows specific immunoprecipitation of activated kinases from transfected cells. The skilled practitioner will recognize that the Glu-tag fusion is not necessary to the invention and that similar results could be obtained with antibodies specific to each or both of the activated variants in the absence of a fusion epitope.

The skilled practitioner will recognize that binding partners or polypeptides that preferentially bind to activated p70β$^{S6K}$ can be isolated by one or more standard techniques such as immunoprecipitation, hplc, fplc, column chromatography or preparative electrophoresis.

Although the present invention has been described in detail with reference to examples above, it is understood that various modifications can be made without departing from the spirit of the invention. Accordingly, the invention is limited only by the following claims. All cited patents and publications referred to in this application are herein incorporated by reference in their entirety.

What is claimed:

1. An isolated polypeptide comprising an amino acid sequence selected from the group consisting of:
   (a) the amino acid sequence of SEQ ID NO: 2;
   (b) amino acids 14 to 495 of SEQ ID NO: 2; and
   (c) an amino acid sequence having at least ninety-five (95) percent sequence identity to SEQ ID NO: 2, wherein the polypeptide phosphorylates a ribosomal S6 protein.

2. The isolated polypeptide of claim 1, wherein the polypeptide comprises the amino acid sequence of SEQ ID NO: 2.

3. The isolated polypeptide of claim 1, wherein the polypeptide consists of the amino acid sequence of SEQ ID NO: 2.

4. The isolated polypeptide of claim 1, wherein the polypeptide comprises amino acids 14 to 495 of SEQ ID NO: 2.

5. The isolated polypeptide of claim 1, wherein the polypeptide consists of amino acids 14 to 495 of SEQ ID NO: 2.

6. The isolated polypeptide of claim 1, wherein the polypeptide comprises an amino acid sequence having at least ninety-five (95) percent sequence identity to SEQ ID NO: 2.

7. The isolated polypeptide of claim 1, wherein the polypeptide contains a substitution of Threonine for Aspartic Acid at residue 401 of the amino acid sequence of SEQ ID NO: 2.

8. An isolated polypeptide encoded by a nucleic acid molecule comprising the entire contiguous open reading frame of SEQ ID NO: 1.

9. The isolated polypeptide of claim 1, wherein the polypeptide is encoded by a nucleic acid molecule having a substitution at a position corresponding to nucleotides 1277, 1278 or 1279 of SEQ ID NO: 1.

10. A fusion protein comprising a polypeptide having the amino acid sequence of SEQ ID NO: 2 fused to a heterologous protein.

11. A fusion protein comprising a polypeptide according to claim 1 fused to a heterologous protein.

* * * * *

UNITED STATES PATENT AND TRADEMARK OFFICE
CERTIFICATE OF CORRECTION

| | | |
|---|---|---|
| PATENT NO. | : 7,998,718 B2 | Page 1 of 1 |
| APPLICATION NO. | : 11/004840 | |
| DATED | : August 16, 2011 | |
| INVENTOR(S) | : Gout et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1454 days.

Signed and Sealed this
Thirty-first Day of January, 2012

David J. Kappos
*Director of the United States Patent and Trademark Office*